(12) United States Patent
Fernyhough et al.

(10) Patent No.: US 11,925,649 B2
(45) Date of Patent: Mar. 12, 2024

(54) TREATMENTS FOR DIABETIC NEUROPATHY

(71) Applicants: University of Manitoba, Winnipeg (CA); University Health Network, Toronto (CA); THE REGENTS OF THE UNIVERSITY OF CALIFORNIA, Oakland, CA (US)

(72) Inventors: Paul Fernyhough, Winnipeg (CA); Nigel A. Calcutt, La Jolla, CA (US); Lakshmi Kotra, Toronto (CA)

(73) Assignees: University of Manitoba, Winnipeg (CA); University Health Network, Toronto (CA); The Regents of the university of California, Oakland, CA (US)

( * ) Notice: Subject to any disclaimer, the term of this patent is extended or adjusted under 35 U.S.C. 154(b) by 0 days.

(21) Appl. No.: 16/160,403

(22) Filed: Oct. 15, 2018

(65) Prior Publication Data

US 2019/0046540 A1   Feb. 14, 2019

Related U.S. Application Data

(62) Division of application No. 13/877,619, filed as application No. PCT/CA2011/001186 on Oct. 24, 2011, now Pat. No. 10,307,428.

(60) Provisional application No. 61/531,803, filed on Sep. 7, 2011, provisional application No. 61/406,502, filed on Oct. 25, 2010.

(51) Int. Cl.
| | |
|---|---|
| *A61K 31/5513* | (2006.01) |
| *A61K 31/46* | (2006.01) |
| *A61K 31/496* | (2006.01) |
| *A61K 31/5517* | (2006.01) |
| *C07D 417/12* | (2006.01) |

(52) U.S. Cl.
CPC .......... *A61K 31/5513* (2013.01); *A61K 31/46* (2013.01); *A61K 31/496* (2013.01); *A61K 31/5517* (2013.01); *C07D 417/12* (2013.01)

(58) Field of Classification Search
CPC ............ A61K 31/5513; A61K 31/5517; A61K 31/46; A61K 31/496; C07D 417/12; A61P 25/02
See application file for complete search history.

(56) References Cited

U.S. PATENT DOCUMENTS

| | | |
|---|---|---|
| 6,512,010 B1 | 1/2003 | Gale |
| 6,841,539 B1 | 1/2005 | Mehta |
| 2003/0064040 A1 | 4/2003 | Lukacsko |
| 2003/0104041 A1 | 6/2003 | Hsu |
| 2004/0137069 A1 | 7/2004 | Takruri |
| 2007/0116730 A1 | 5/2007 | Simmons |
| 2007/0293480 A1 | 12/2007 | Seed |
| 2007/0293481 A1* | 12/2007 | Seed ..................... A61K 31/343 514/220 |
| 2008/0255062 A1 | 10/2008 | Fernyhough |

FOREIGN PATENT DOCUMENTS

| | | |
|---|---|---|
| WO | WO 2007/025613 A2 | 3/2007 |
| WO | WO 2007/147123 | 12/2007 |

OTHER PUBLICATIONS

Lynch, et al., Topical Amitriptyline and Ketamine in Neuropathic Pain Syndromes: Open-Label Study, Journal of Saunders, Philadelphia, PA, US, vol. 6, No. 10, Oct. 1, 2005 (Oct. 1, 2005).
Ulugol, Ahmet, et al., Involvement of adenosine in the antiallodynic effect of amitriptyline in streptozotocin-induced diabetic rats. Neuroscience Letters, Aug. 9, 2002, vol. 328, No. 2, Aug. 9, 2002 (Aug. 9, 2002).
Soren H. Sindrup, et al., Antidepressants in the Treatment of Neuropathic Pain, Basic & Clinical Pharmacology & Toxicology, vol. 96, 2005, pp. 399-409.
R. Van der Ploeg et al., Development of 1-10 Therapeutic Candidates to Treat Diabetic Sensory Neuropathy, May 2008 (May 2008).
Chen Shao-Rui, et al., Up-regulation of spinal muscarinic receptors and increased antinociceptive effect of intrathecal muscarine in diabetic rats. The Journal of Pharmacology and Experimental Therapeutics Nov. 2003, vol. 307, No. 2, Nov. 2003 (Nov. 2003), pp. 676-681.
Hwang J-H, et al, The Antiallodynic Effects of Intrathecal Cholinesterase Inhibitors in a Rat Model of Neuropathic Pain. Anesthesiology, American Society Of Anesthesiologists, Philadelphia, PA, US, vol. 90, No. 2, Feb. 1, 1999 (Feb. 1, 1999).
Jang, S.W., et al., Amitriptyline is a TrkA and TrkB Receptor Agonist that Promotes TrkA/TrkB Heterodimerization and Has Potent Neurotrophic Acti vity11, Chemistry and Biology, Current Biology, London, GB, vol. 16, No. 6, Jun. 26, 2009 (Jun. 26, 2009).
K. L. Vandemark, et al., The Activation of MI Muscarinic Receptor Signaling Induces Neuronal Differentiation in Pyramidal Hippocampal Neurons, Journal of Pharmacology and Experimental Therapeutics, vol. 329, No. 2, May 1, 2009 (May 1, 2009).

(Continued)

*Primary Examiner* — Sahar Javanmard
(74) *Attorney, Agent, or Firm* — Knobbe Martens Olson & Bear LLP

(57) ABSTRACT

Treatments for therapy of a diabetic symmetrical polyneuropathy a subject in need thereof. The treatments includes administration of compositions comprising: an effective amount of a muscarinic acetylcholine receptor antagonist exemplified by pirenzepine, telenzepine, atropine, or derivatives thereof or salts thereof or analogs thereof or derivatives thereof, and a pharmacologically acceptable carrier. The composition may be injectable or alternatively, may be applied topically or alternatively, may be delivered orally. A suitable topical composition may comprise a lotion, a cream, a gel, or a viscous fluid. The muscarinic acetylcholine receptor antagonist may be a muscarinic acetylcholine receptor antagonist salt or a muscarinic acetylcholine receptor antagonist derivative or a muscarinic acetylcholine receptor antagonist analog.

27 Claims, 19 Drawing Sheets

(56) References Cited

OTHER PUBLICATIONS

Nigel A. Calcutt, et al. Selective antagonism of muscarinic receptors is neuroprotective in peripheral neuropathy, Journal of Clinical Investigation, vol. 127, No. 2, Feb. 1, 2017 (Feb. 1, 2017), pp. 608-622.

Sheffler et al, A Novel Selective Muscarinic Acetylcholine Receptor Subtype 1 Antagonist Reduces Seizures Without Impairing Hippocampus-Dependent Learning; 2009; pp. 356-368; vol. 76, No. 2.

International Search Report and the Written Opinion of the International Searching Authority received with respect to related PCT International Patent Application No. PCT/CA2011/001186.

* cited by examiner

Mice at 14wk exhibited approximately 40% loss in IENF in skin. Pirenzepine treatment (daily 10mg/kg sc) initiated at this point and maintained for 2 months.

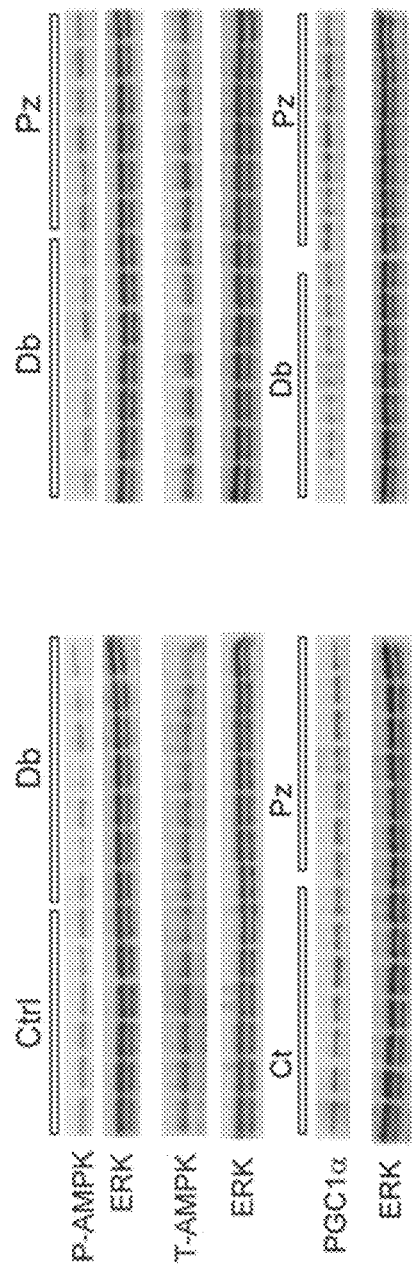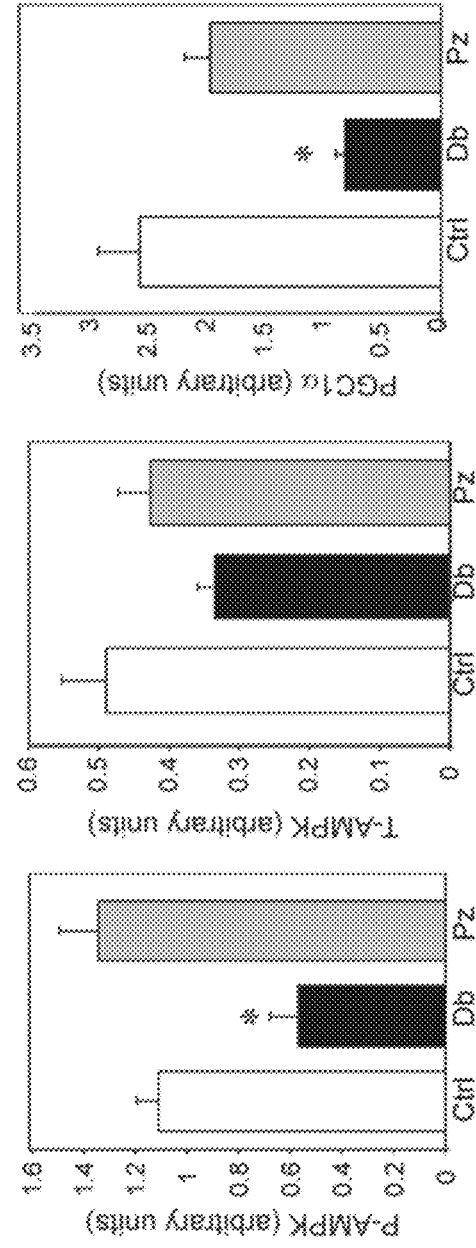
Fig. 16(A)
Fig. 16(B)
Fig. 16(C)
Fig. 16(D)

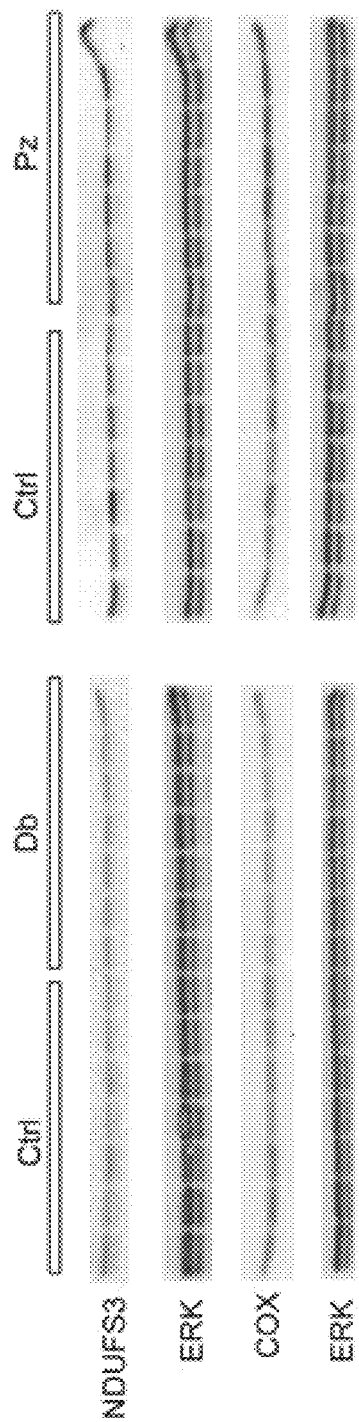
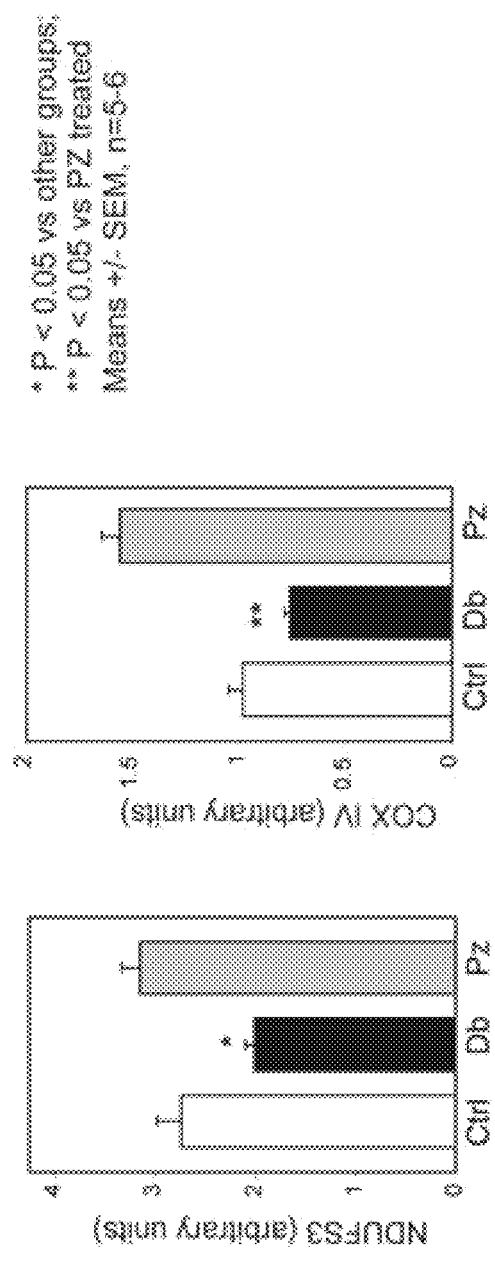
Fig. 17(A)
Fig. 17(B)
Fig. 17(C)

TREATMENTS FOR DIABETIC NEUROPATHY

CROSS-REFERENCE TO RELATED APPLICATIONS

The present application is a divisional application of U.S. patent application Ser. No. 13/877,619 filed on Jun. 17, 2013, which is a national phase application under 35 U.S.C. § of International Patent Application No. PCT/CA2011/001186, filed Oct. 24, 2011, which claims priority to U.S. Provisional Application No. 61/531,803, filed Sep. 7, 2011, and U.S. Provisional Application No. 61/406,502, filed Oct. 25, 2010. The entire contents of these applications are incorporated by reference.

Any and all applications for which a foreign or domestic priority claim is identified in the Application Data Sheet as filed with the present application are hereby incorporated by reference under 37 CFR 1.57.

FIELD OF THE INVENTION

This invention relates to therapies for diabetic symmetrical polyneuropathy. More particularly, this invention relates to therapeutic compositions for distal symmetrical polyneuropathy, wherein the compositions comprise an effective amount of a muscarinic acetylcholine receptor antagonist or a salt or derivative thereof.

BACKGROUND

Symmetrical polyneuropathy is a clinical problem in about 50% of persons affected with diabetes. The clinical symptoms may include development of upper back and/or abdominal pain (i.e., diabetic thoracoabdominal neuropathy), loss of control of eye movements (i.e., third-nerve palsy), and progressive loss of function of the nerves comprising the peripheral nervous system (e.g., polyneuropathy, mononeuropathy, mononeuritis simplex, autonomic neuropathy).

The dominant form of diabetic neuropathy presents as a distal symmetrical polyneuropathy that initially affects subjects' feet, legs and hands. The primary symptoms include loss of touching and/or feeling sensations and the loss of ability to sense pain-causing stimuli. A sub-group of patients with early diabetic neuropathy also develop positive symptoms of neuropathic pain such as inappropriate tingling, burning, shooting or aching sensations that may co-exist with other negative symptoms of sensory loss. Such neuropathic pain is commonly referred to as tactile allodynia or mechano-hyperalgesia.

Distal sensory neuropathy can be measured using skin biopsies to determine loss of intraepidermal nerve fibers (IENF). IENF loss represents retraction of sensory neuron nerve endings from the epidermis with subsequent sensory loss that ultimately contributes to high incidences of ulceration, gangrene and amputation in subjects suffering advanced diabetes. Currently, there are no regulatory approved therapies available in North America for this degenerative symmetrical polyneuropathy. The current costs to health systems for providing relief of these symptoms are enormous.

SUMMARY OF THE INVENTION

The exemplary embodiments of the present invention pertain to compositions suitable for therapy of diabetic symmetrical polyneuropathy. The therapeutic compositions comprise one of a muscarinic acetylcholine receptor antagonist, a salt of a muscarinic acetylcholine receptor antagonist, and a derivative of a muscarinic acetylcholine receptor antagonist. The compositions are suitable for treating both the negative symptoms of diabetic symmetrical polyneuropathy exemplified by nerve conduction slowing and by sensory loss, and the positive symptoms of diabetic symmetrical polyneuropathy exemplified by tactile allodynia and by mechano-hyperalgesia.

According to one aspect of the present invention, the muscarinic acetylcholine receptor antagonist compositions are injectable. The injections may be subcutaneous injections into a subject's body. Alternatively, the injections may be sub-epidermal injections. Suitable target injection sites include, among others, toes, feet, ankles, knees and legs. Other suitable target injection sites include, among others, fingers, hands, wrists, arms and shoulders. Yet other suitable target injection sites include the upper and lower back, the chest and the abdominal area.

According to another aspect of the present invention, the muscarinic acetylcholine receptor antagonist compositions are suitable for topical administrations onto selected target sites on a subject's body. Suitable target topical application sites include, among others, toes, feet, ankles, knees and legs. Other suitable target topical application sites include, among others, fingers, hands, wrists, arms and shoulders. Other suitable target topical application sites include the upper and lower back, the chest and the abdominal area. Alternatively, the muscarinic acetylcholine receptor antagonist compositions maybe delivered to selected target sites on a subject's body by transdermal patches.

According to another aspect of the present invention, the muscarinic acetylcholine receptor antagonist compositions are suitable for oral delivery into a subject's body.

If so desired, the injectable compositions of the present invention can be used in combination with, concurrently with, or sequentially with the topical compositions of the present invention and/or in combination with, concurrently with, or sequentially with the oral compositions of the present invention.

Other exemplary embodiments pertain to use of the compositions of the present invention for therapy of diabetic symmetrical polyneuropathy. The use may include injections of dosages comprising effective amounts of a muscarinic antagonist into selected target sites on a subject's body. Alternatively, the use may include topical applications and/or transdermal patch applications of muscarinic acetylcholine receptor antagonist compositions onto selected target sites on a subject's body. Alternatively, the use may include oral delivery of muscarinic acetylcholine receptor antagonist compositions into a subject's body.

Other exemplary methods pertain to methods for manufacturing the injectable compositions of the present invention.

Other exemplary methods pertain to methods for manufacturing the topical compositions of the present invention.

Other exemplary methods pertain to methods for manufacturing the oral compositions of the present invention.

DESCRIPTION OF THE DRAWINGS

The present invention will be described in conjunction with reference to the following drawings in which.

Figure 2A:
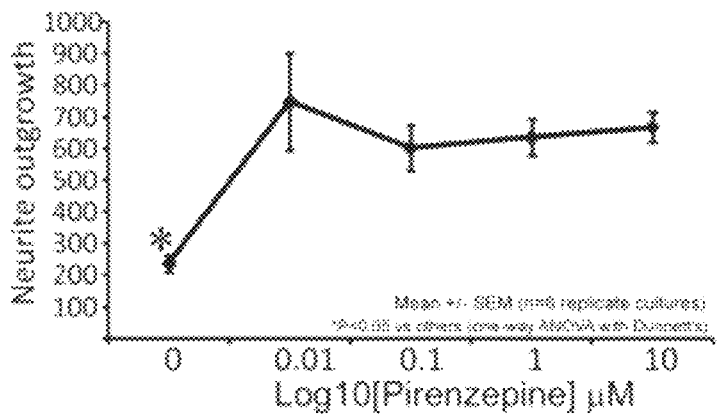
Figure 2B:
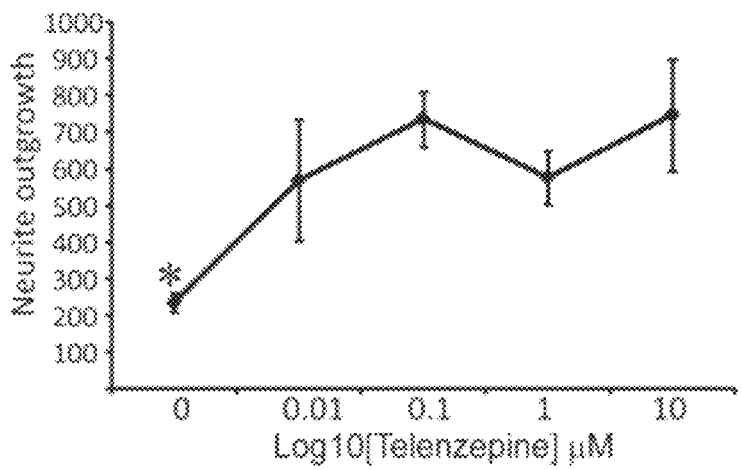
Figure 2C:
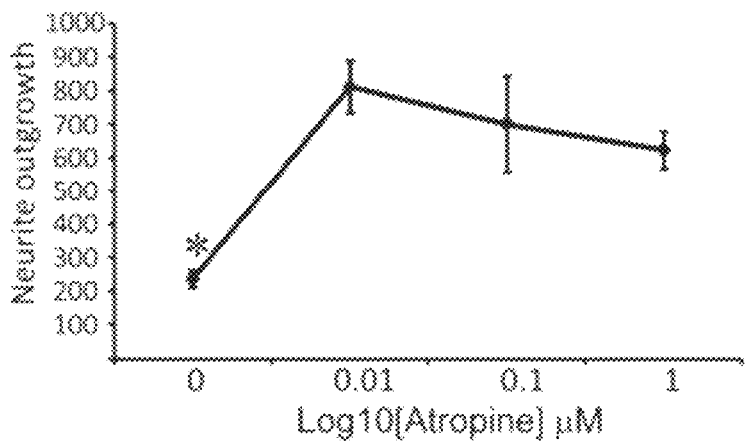
Figure 3:
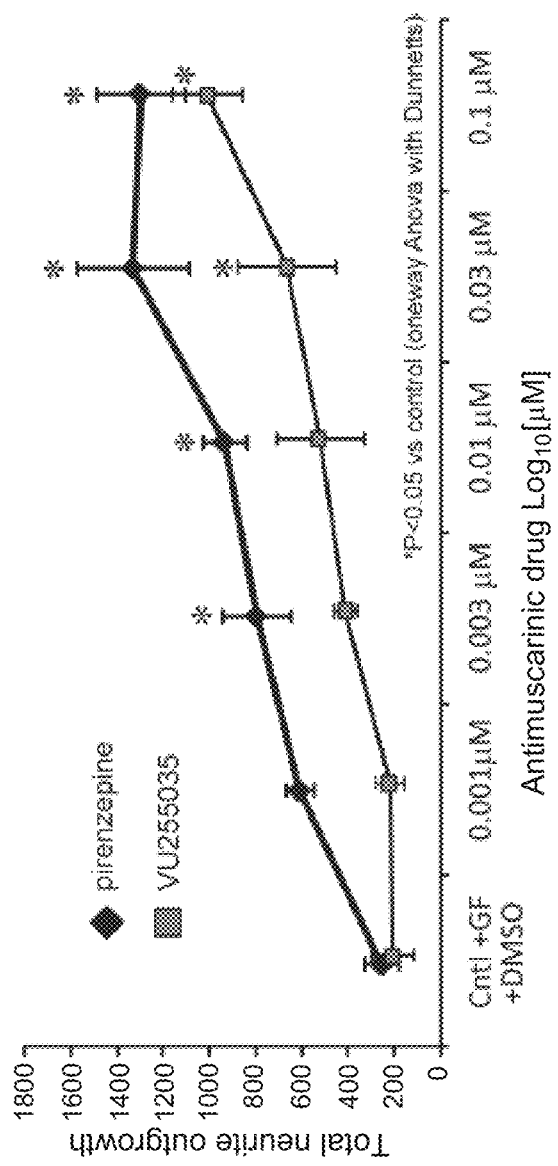
Figure 4:
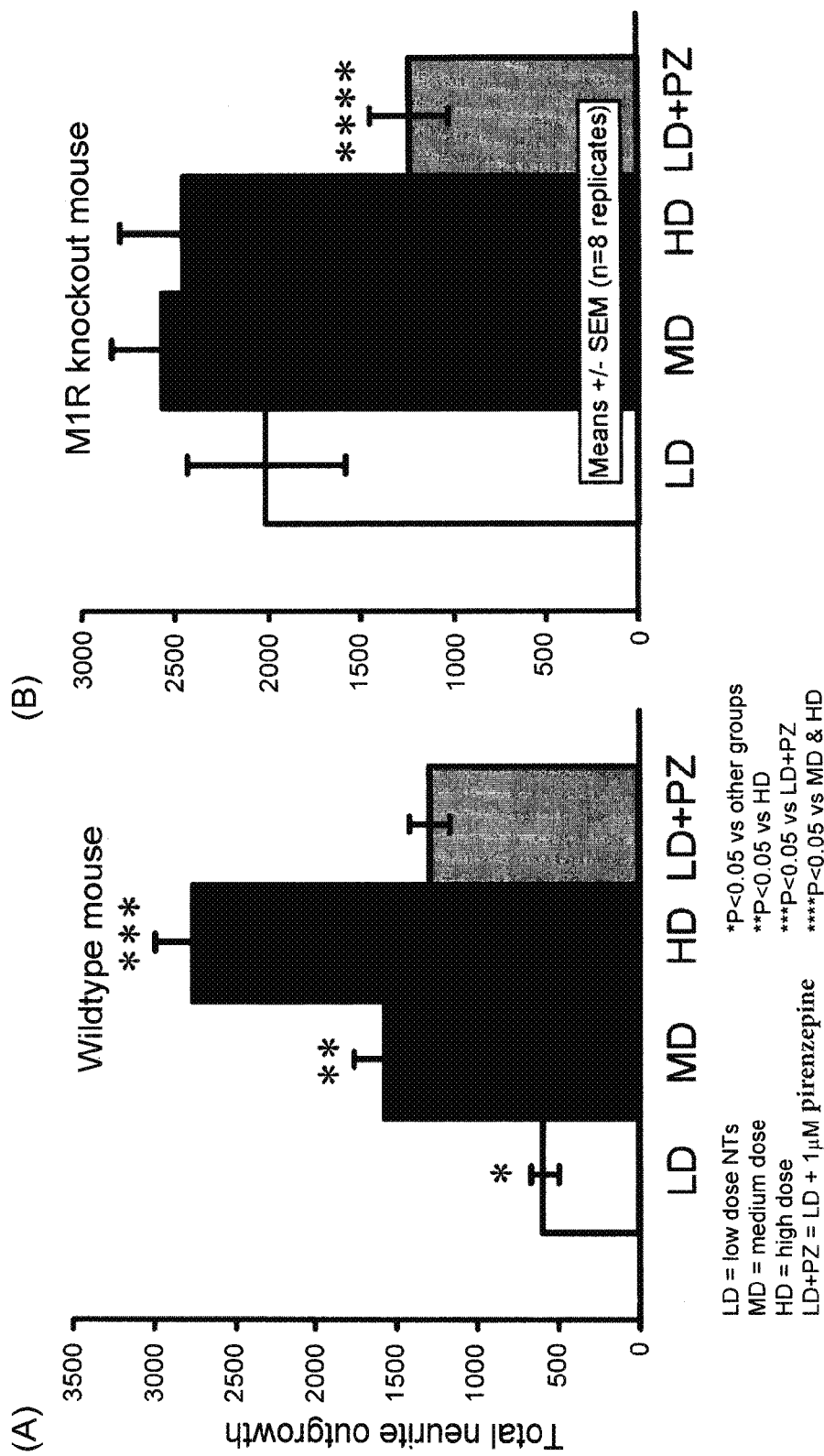
Figure 5:
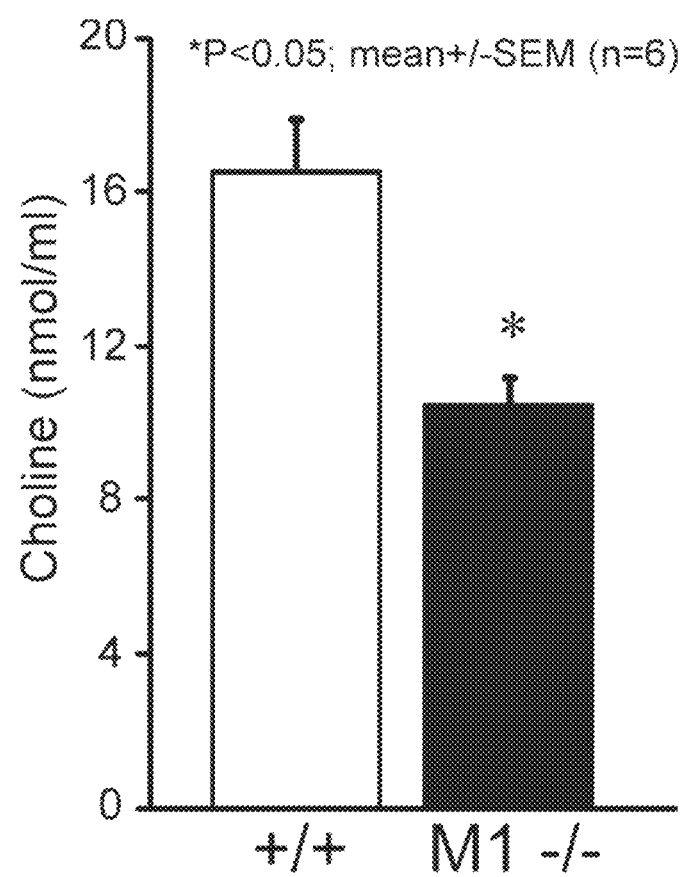
Figure 6A:
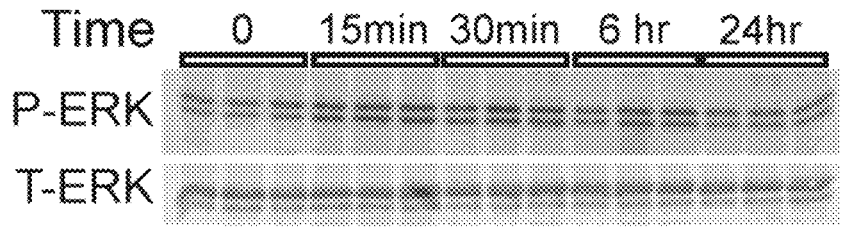
Figure 6B:
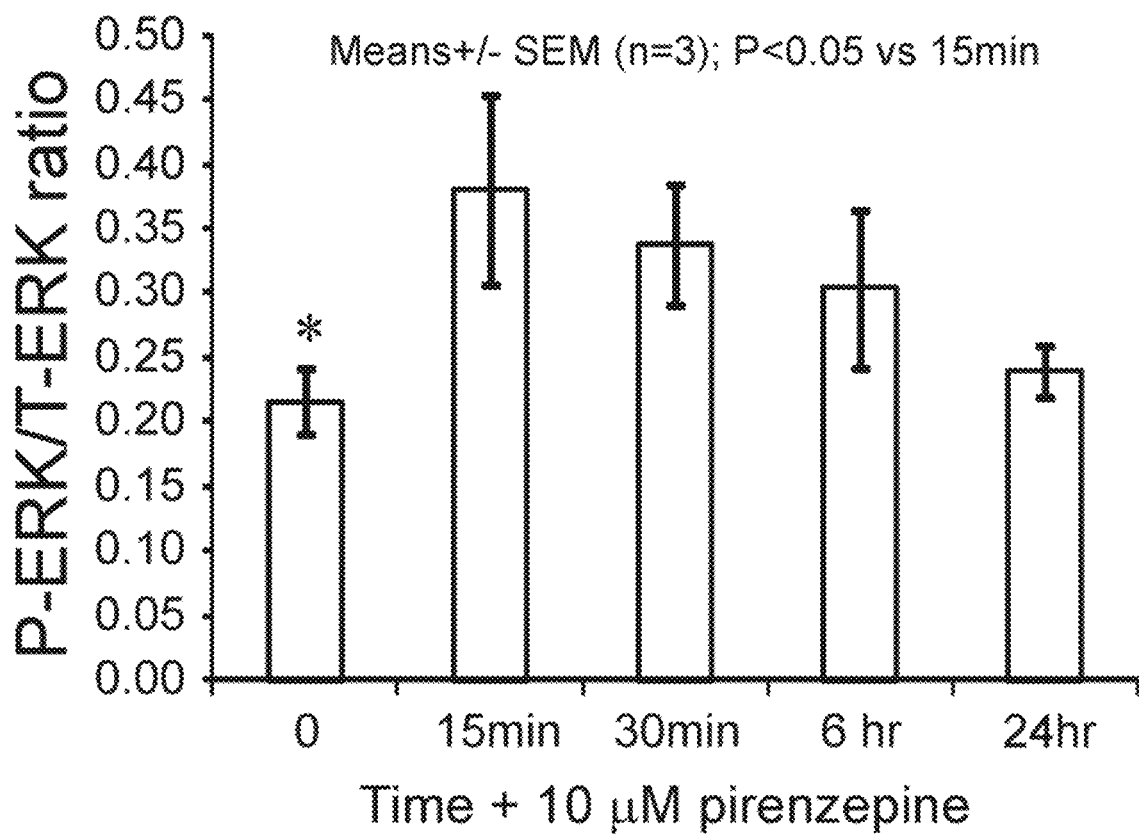
Figure 7A:
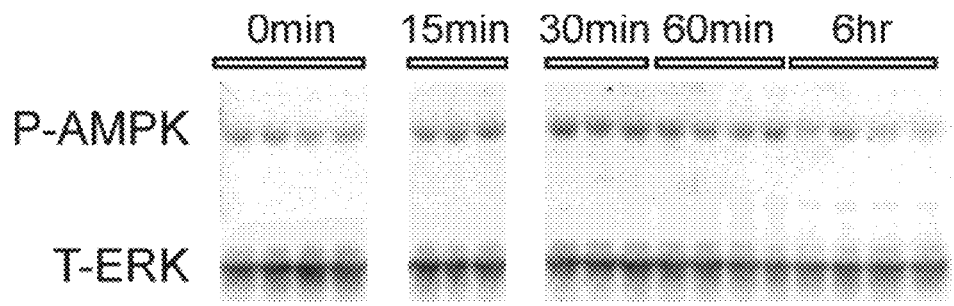
Figure 7B:
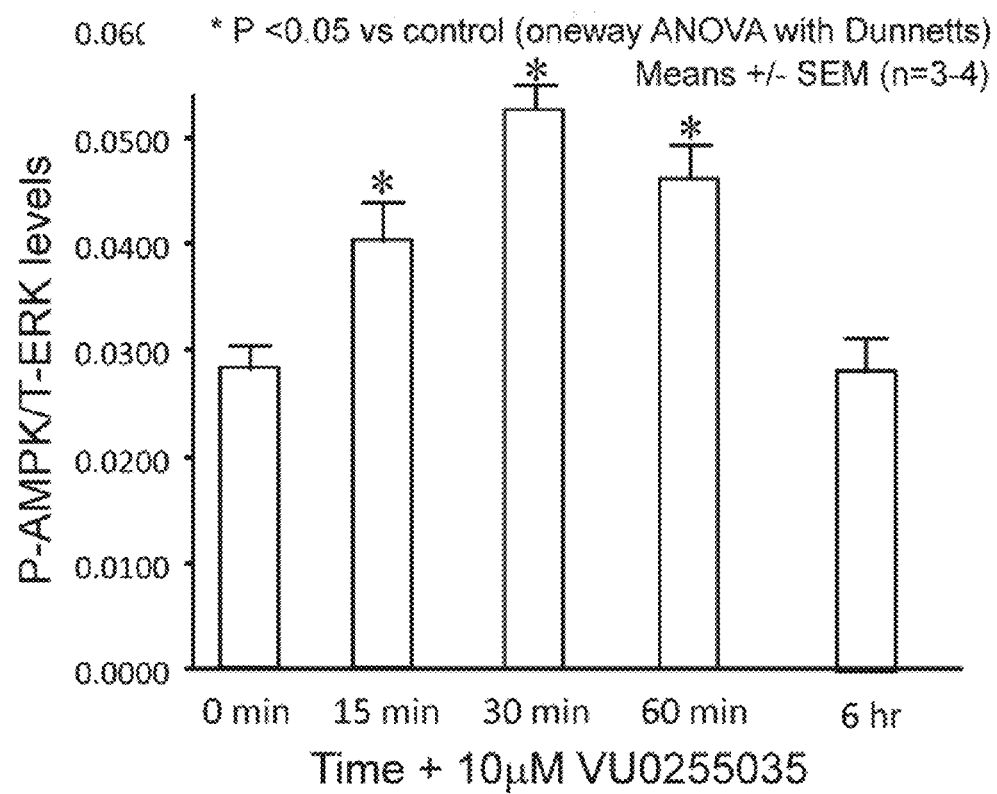
Figure 8A:
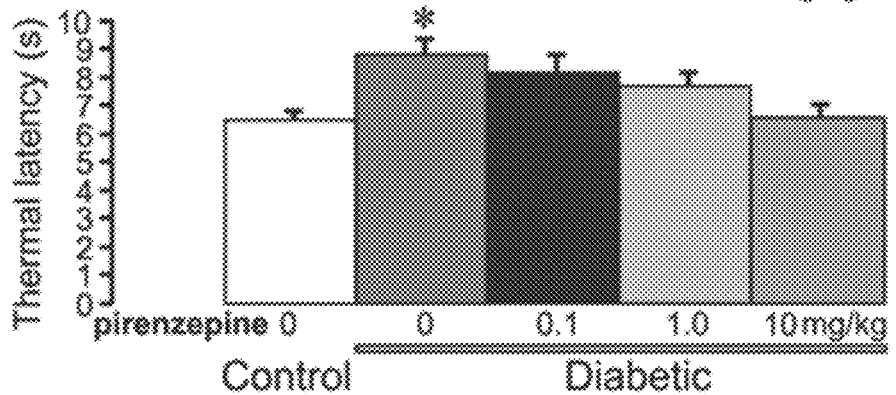
Figure 8B:
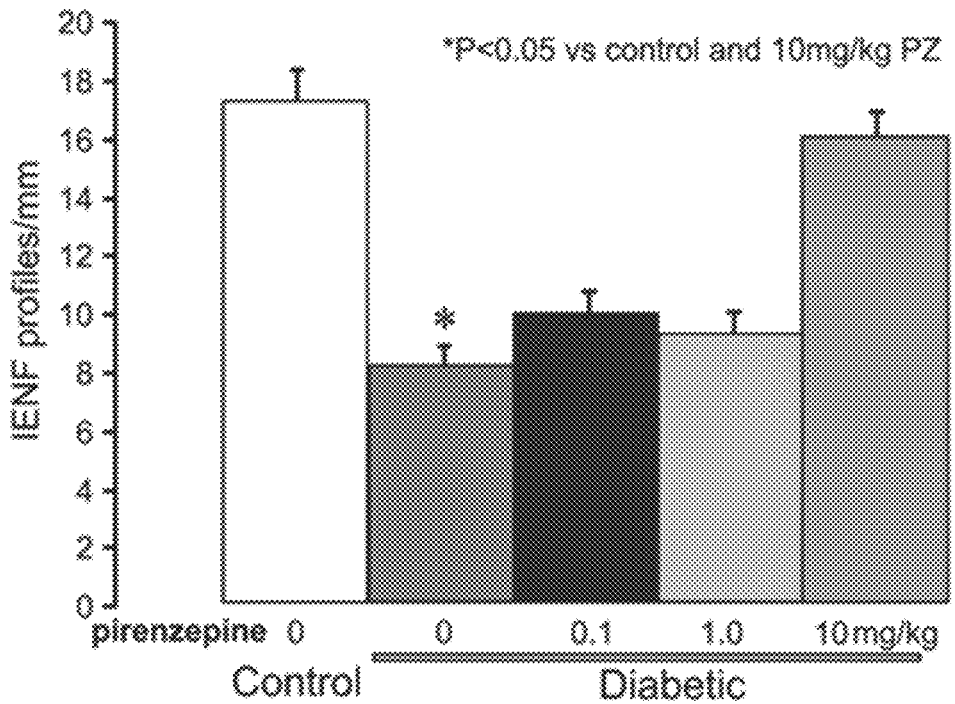
Figure 9A:
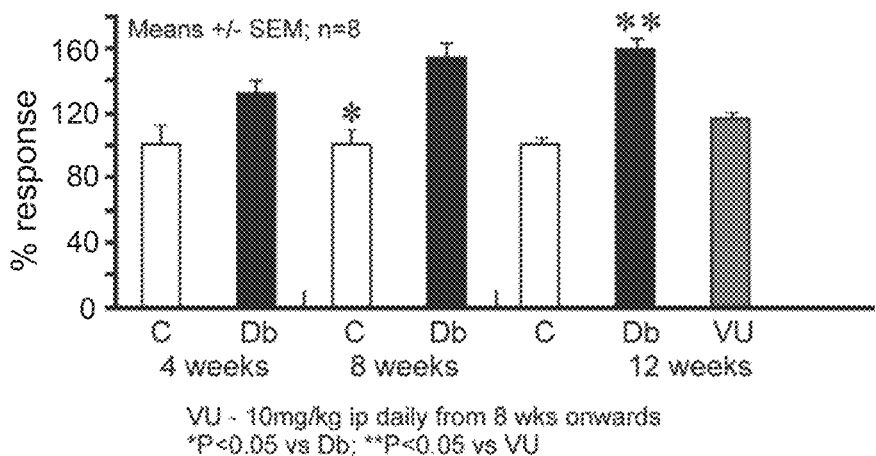
Figure 9B:
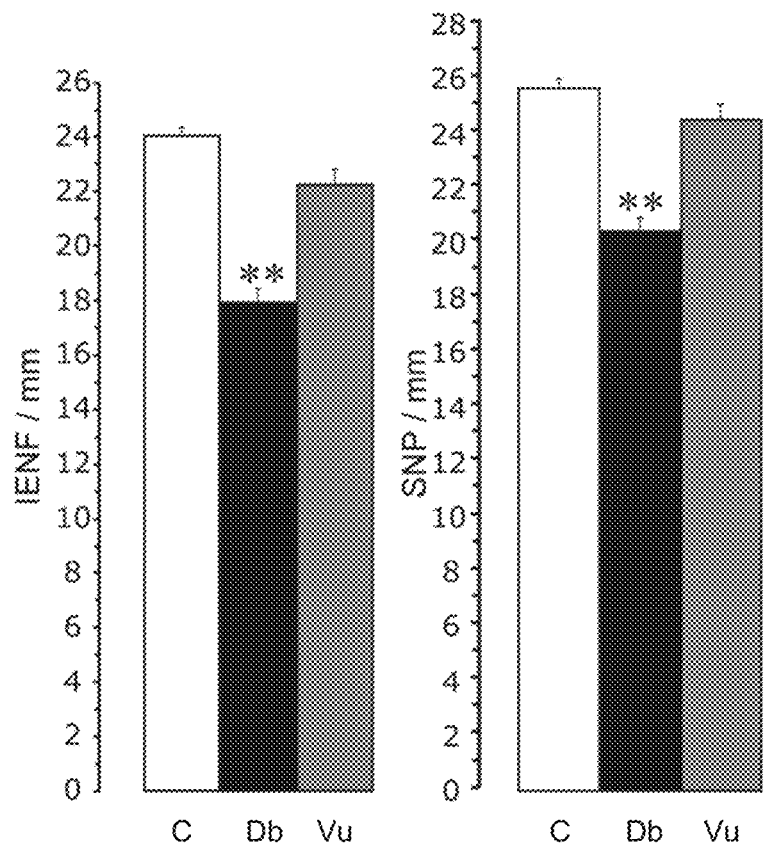
Figure 10A:
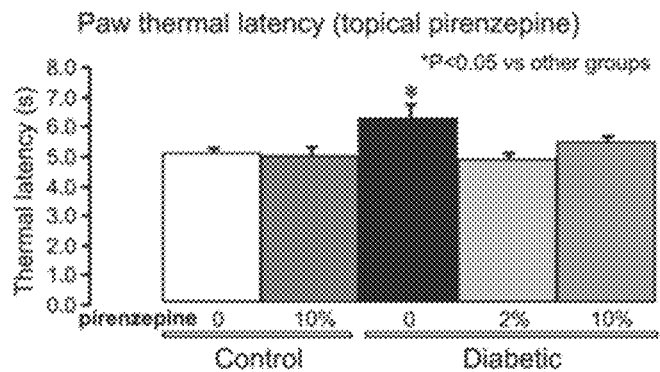
Figure 10B:
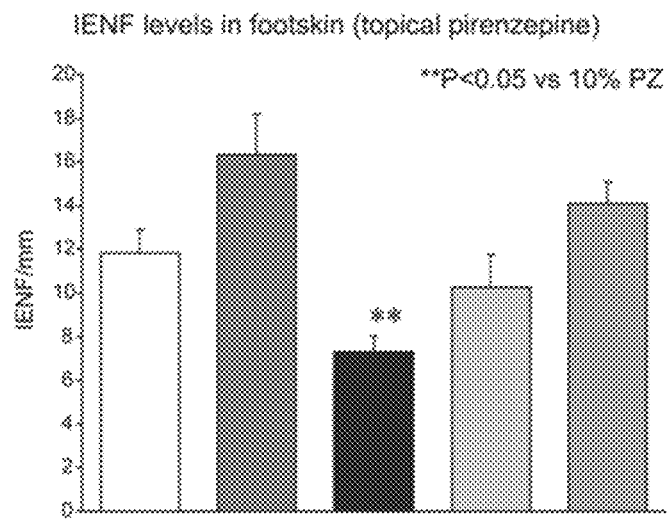
Figure 10C:
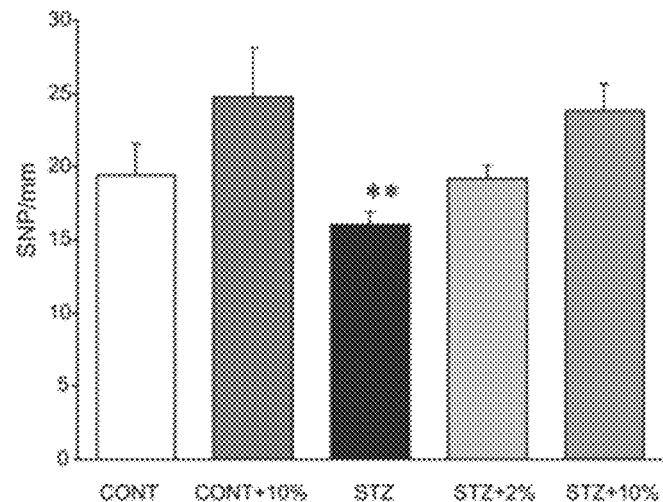
Figure 11A:
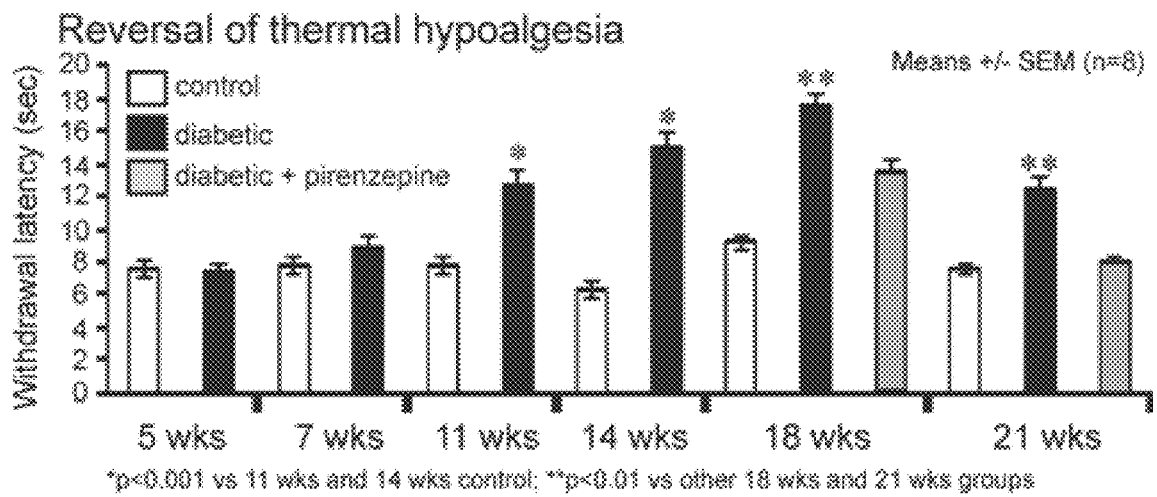
Figure 11B:
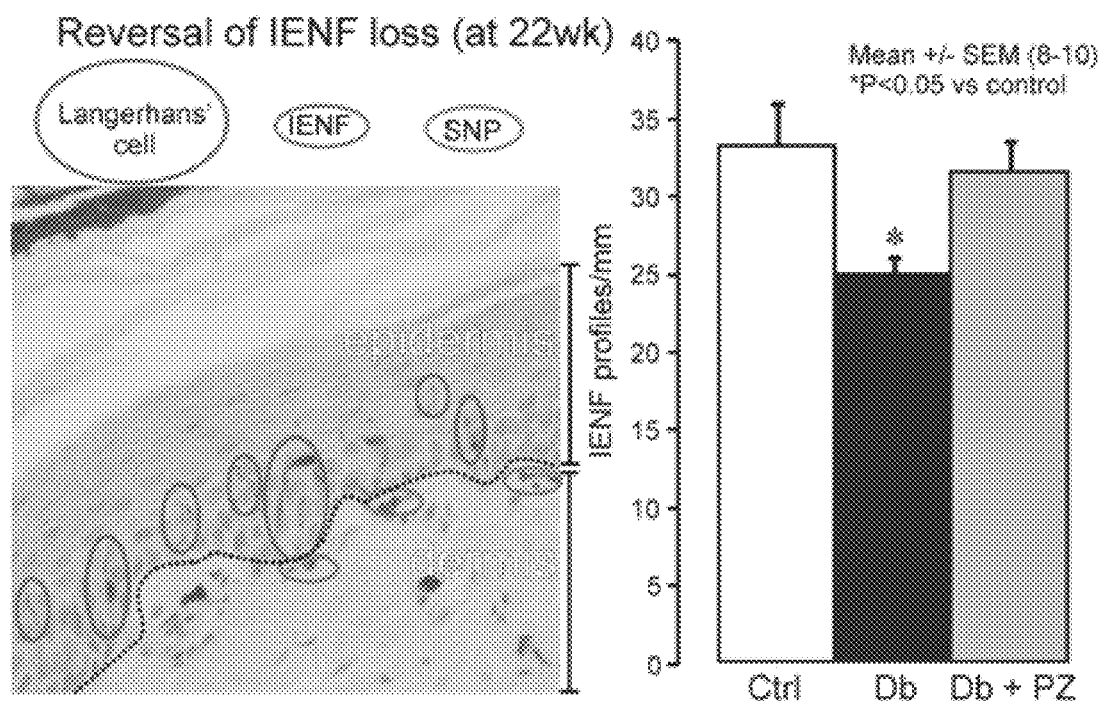
Figure 12:
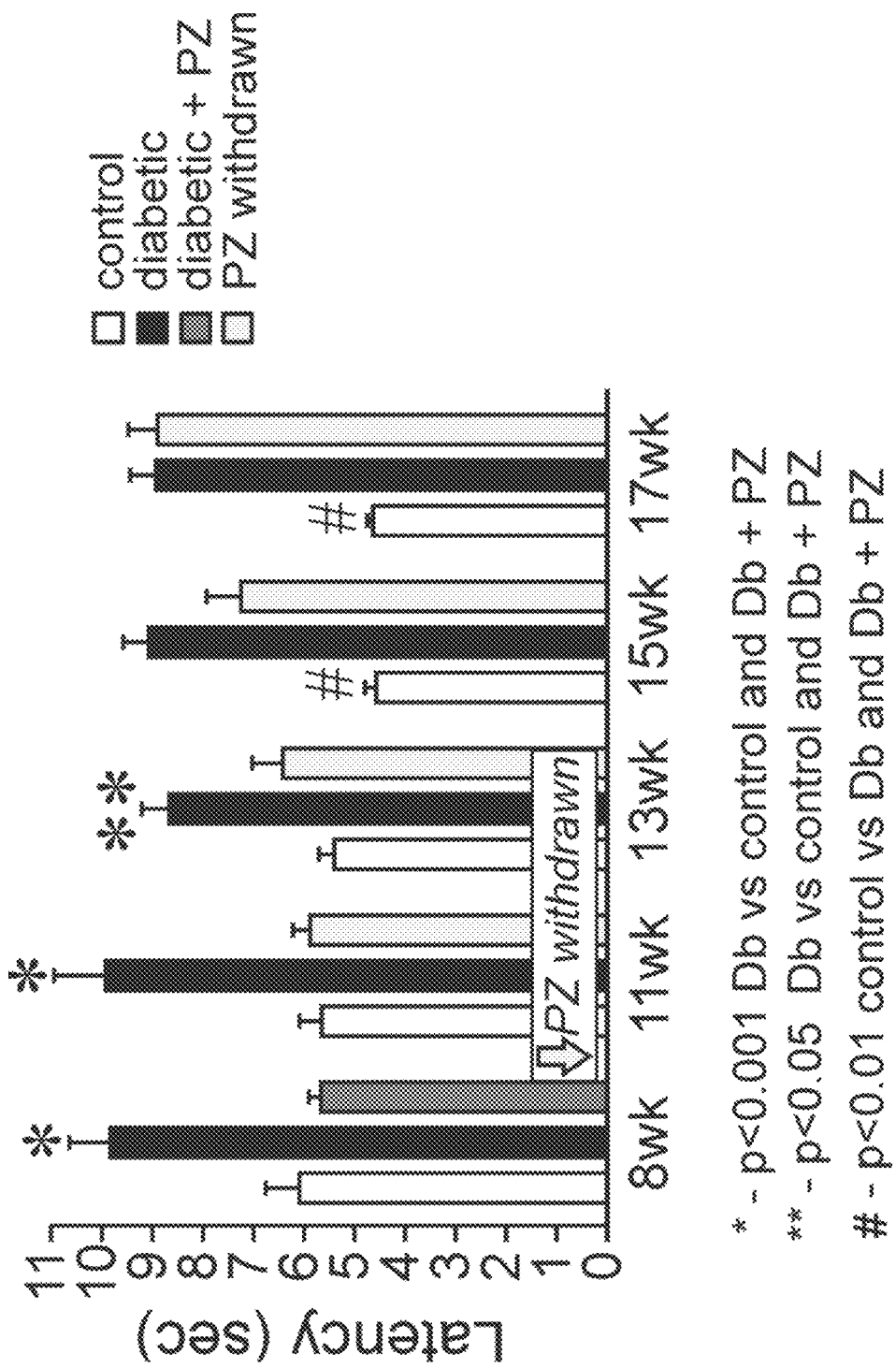
Figure 13:
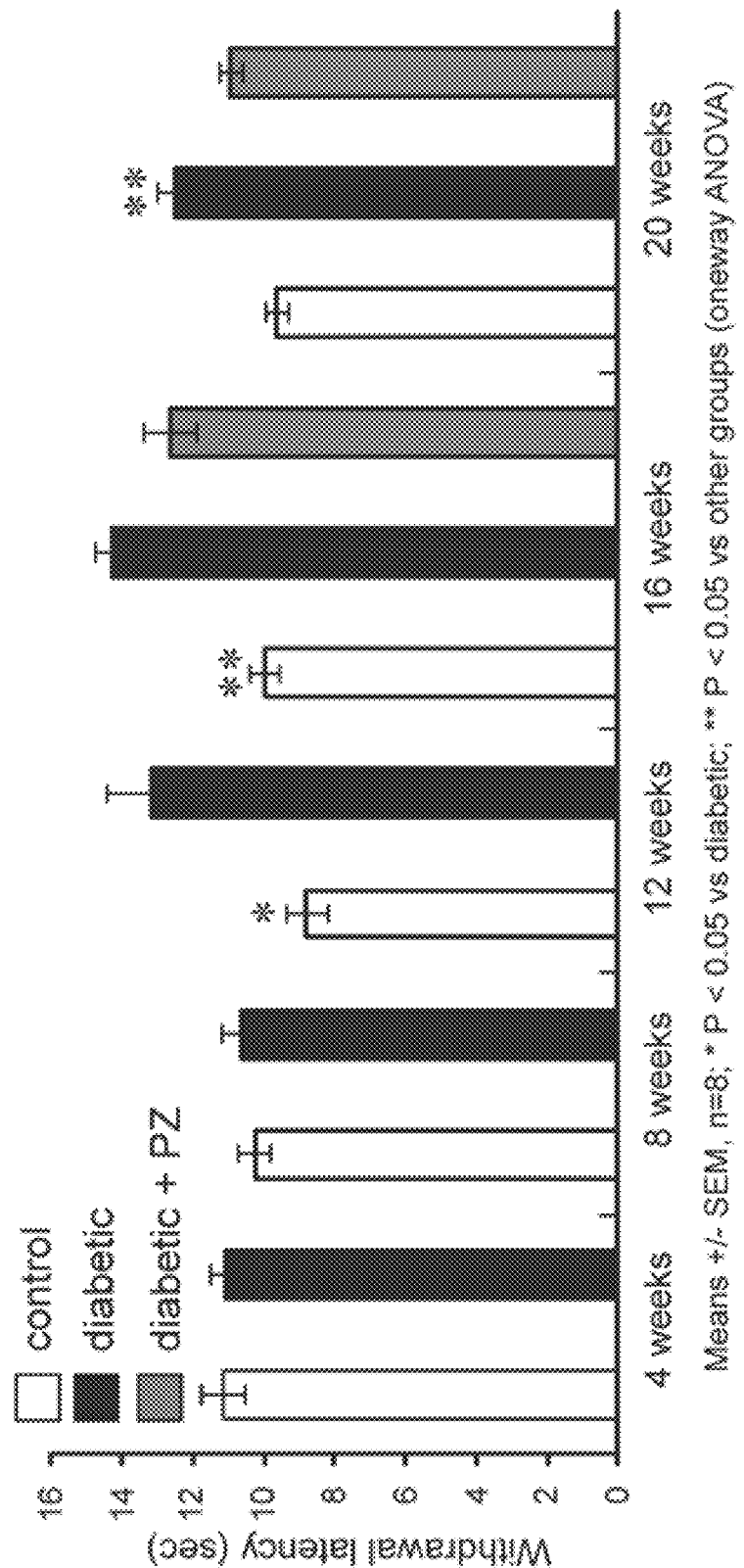
Figure 14A:
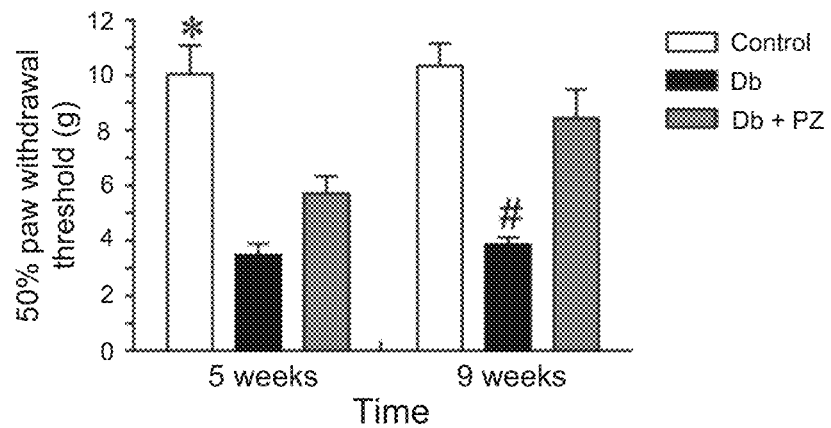
Figure 14B:
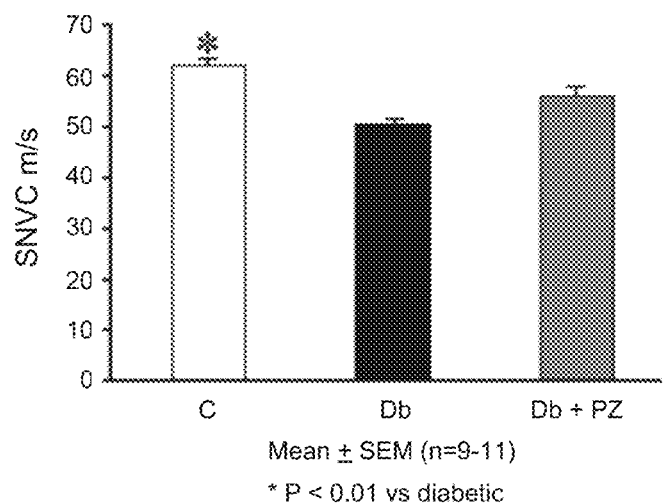
Figure 15A:
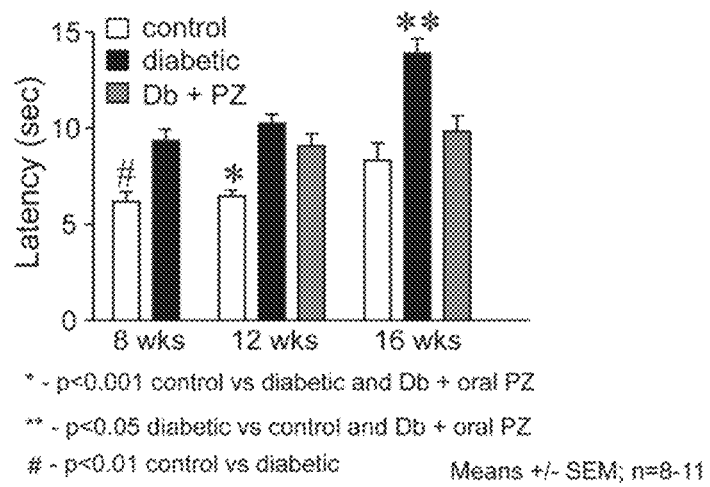
Figure 15B:
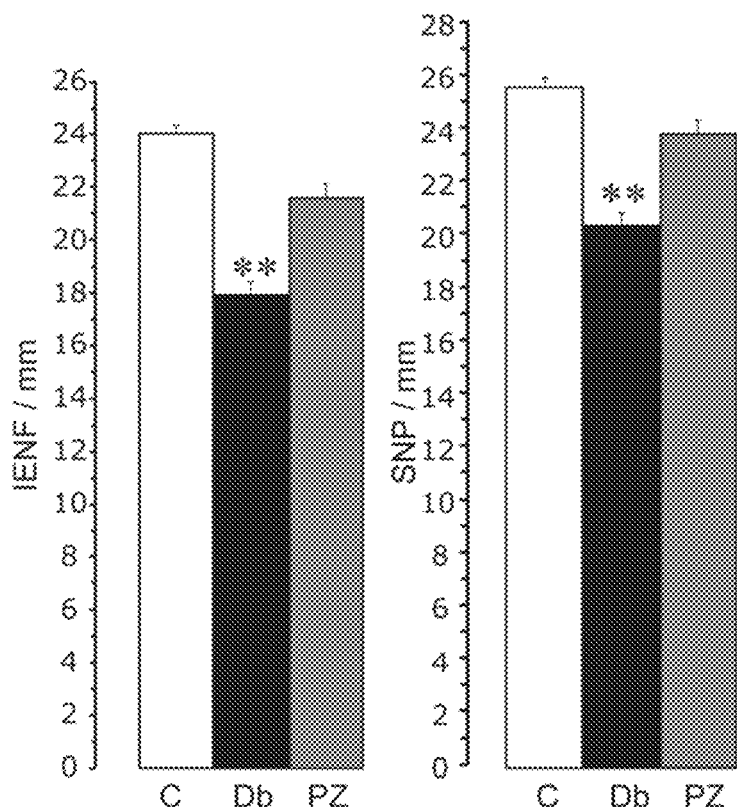
Figure 18A:
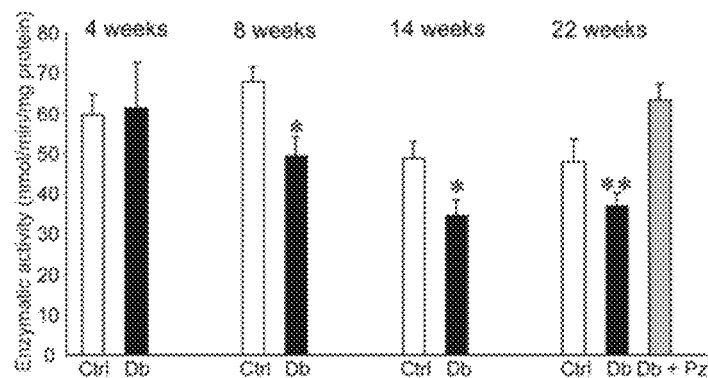
Figure 18B:
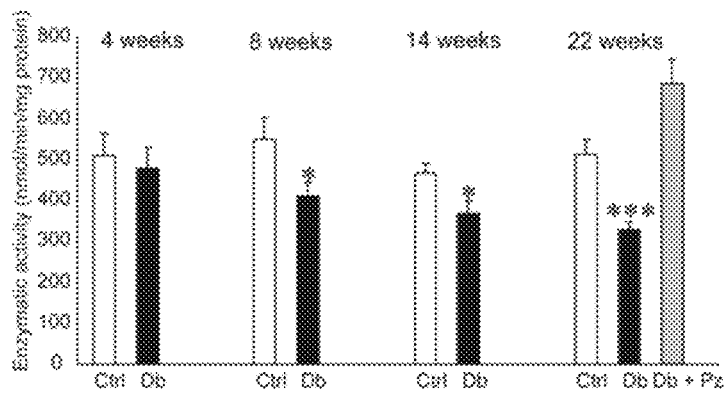
Figure 18C:
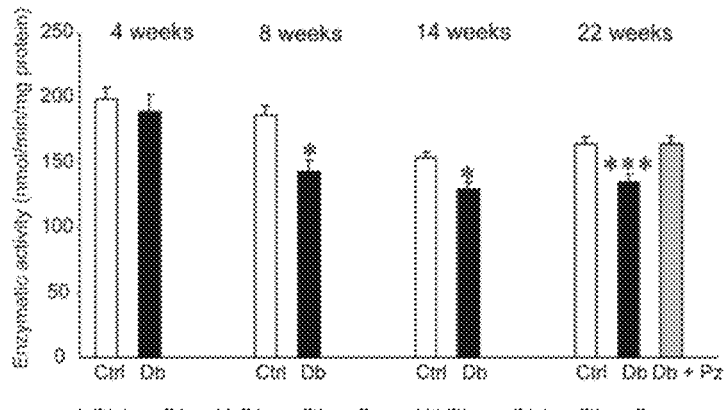
Figure 19:
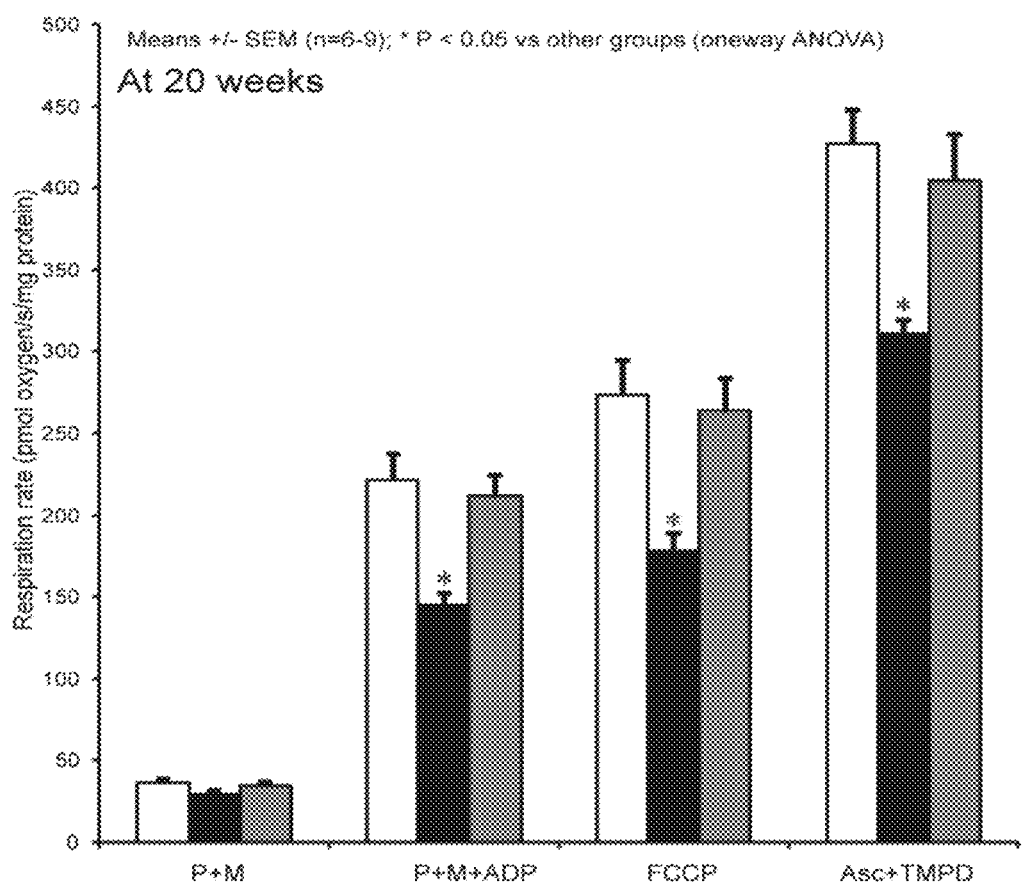

antagonist, on neurons cultured from Zucker diabetic fatty (ZDF) rats (model of type 2 diabetes);

FIGS. 2(A)-2(C) are charts showing the effects of muscarinic acetylcholine receptor antagonists on neurite outgrowth from neurons cultured from normal rats, 2(A) pirenzepine, 2(B) telenzepine, and 2(C) atropine;

FIG. 3 is a chart showing the effects of low doses of muscarinic acetylcholine type 1 receptor (M1R) antagonists on neurite outgrowth from neurons cultured from normal rats;

FIGS. 4(A) and 4(B) show the effects of pirenzepine on neurite outgrowth from sensory neuron cultures isolated from: 4(A) wildtype mice, and 4(B) M1R knockout mice;

FIG. 5 is a chart comparing acetylcholine production in cultures from wildtype mice and in cultures from M1R knockout mice;

FIG. 6(A) is a Western immuno blot analysis showing the effects of pirenzepine on phosphorylation of extracellular-regulated protein kinase (ERK) in cultured sensory neurons, while FIG. 6(B) is a chart showing the effects of pirenzepine on the P-ERK/T-ERK ratio;

FIG. 7(A) is a Western immuno blot analysis showing the effects of VU255035 on phosphorylation of AMP-activated protein kinase (AMPK) in cultured sensory neurons, while FIG. 7(B) is a chart showing the effects of VU255035 on the P-AMPK/T-ERK ratio;

FIGS. 8(A) and 8(B) are charts showing the prophylactic effects of subcutaneous injections of pirenzepine on: 8(A) thermal hypoalgesia and 8(B) loss of intraepidermal nerve fibers (IENF) in streptozotocin (STZ) diabetic C57Bl6J mice (model of type 1 diabetes);

FIGS. 9(A) and 9(B) are charts showing the effects of the specific M1R antagonist VU255035 in reversing 9(A) thermal hypoalgesia, and 9(B) IENF loss in STZ-induced diabetic Swiss Webster mice;

FIGS. 10(A)-10(C) are charts showing the prophylactic effects of topical applications of pirenzepine on: 10(A) thermal hypoalgesia, 10(B) loss of intraepidermal nerve fiber (IENF), and 10(C) sub-epidermal nerve plexi (SNP) in STZ diabetic C57Bl6J mice;

FIGS. 11(A) and 11(B) are charts showing the effects of long-term subcutaneous injections of pirenzepine in reversing: 11(A) thermal hypoalgesia, and 11(B) loss of IENF in out-bred Swiss-Webster diabetic mice;

FIG. 12 is a chart showing the effects of withdrawal of pirenzepine treatments on reappearance of neuropathy;

FIG. 13 is a chart showing the effects of pirenzepine injections on reversal of thermal hypoalgesia in STZ diabetic Sprague-Dawley rats;

FIG. 14(A) is a chart showing that daily sub-cutaneous administration of pirenzepine prevents paw tactile allodynia in STZ-diabetic Sprague-Dawley rats after 5 or 9 weeks of treatment and thus prevents onset of painful diabetic neuropathy, and FIG. 14(B) is a chart showing the effects of pirenzepine on development of sensory nerve conduction velocity in the same animals, measured after 8 weeks of diabetes;

FIGS. 15(A) and 15(B) are charts showing the effects of oral pirenzepine dosing on reversal of: 15(A) paw thermal hypoalgesia, and 15(B) loss of IENF in STZ-diabetic Swiss Webster mice;

FIG. 16(A) is a Western immuno blot analysis showing the effects of pirenzepine on preserving the expression of AMP-activated protein kinase (AMPK) and peroxisome proliferator-activated receptor/coactivator-1α (PGC-1α), FIG. 16(B) is a chart showing the effects of pirenzepine on P-AMPK expression, FIG. 16(C) is a chart showing the effects of pirenzepine on T-AMPK levels, and FIG. 16(D) is a chart showing the effects of pirenzepine on PGC-la expression in STZ diabetic mice;

FIG. 17(A) is a Western immuno blot analysis showing the effects of pirenzepine on reversing deficits in expression of mitochondrial proteins NDUFS3 and COX IV (T-ERK is measured as a loading control), FIG. 17(B) is a chart showing the effects of pirenzepine on expression of the NDUFS3 protein, and FIG. 17(C) is a chart showing the effects of pirenzepine on expression of the COX IV protein in STZ diabetic mice;

FIGS. 18(A), 18(B), and 18(C) are bar charts showing the effects of pirenzepine on reversing deficits in the activities of mitochondrial respiratory complex I shown in FIG. 18(A), mitochondrial respiratory complex IV shown in FIG. 18(B), and mitochondrial citrate synthase shown in FIG. 18(C) in STZ diabetic mice; and FIG. 19 is a bar chart showing the effects of daily sub-cutaneous pirenzepine injections on restoration of mitochondrial respiratory chain activity in freshly homogenized lumbar dorsal root ganglia of STZ-diabetic rats.

DETAILED DESCRIPTION OF THE PREFERRED EMBODIMENT

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the meanings that would be commonly understood by one of skill in the art in the context of the present specification. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural references unless the context clearly dictates otherwise. Thus, for example, reference to "a muscarinic acetylcholine receptor antagonist" includes a plurality of such muscarinic acetylcholine receptor antagonists and reference to "the agent" includes reference to one or more agents and equivalents thereof known to those skilled in the art, and so forth.

"Optional" or "optionally" or "alternatively" means that the subsequently described event, circumstance, or material may or may not occur or be present, and that the description includes instances where the event, circumstance, or material occurs or is present and instances where it does not occur or is not present.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also, encompassed within the invention, subject to any specifically excluded limit in the stated range. Where the stated range includes one or both of the limits, ranges excluding either or both of those included limits are also included in the invention.

Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between the specifically recited percentages, as compared to native or control levels.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the increase in an activity, response, condition, disease, or other biological parameter can be a 10, 20, 30, 40, 50, 60, 70, 80, 90, 100%, or more, including any amount of increase in between the specifically recited percentages, as compared to native or control levels.

As used herein, the term "subject" means any target of administration. The subject can be a vertebrate, for example, a mammal. Thus, the subject can be a human. The term does not denote a particular age or sex. Thus, adult, juvenile, and newborn subjects, whether male or female, are intended to be covered. A patient refers to a subject afflicted with a disease or disorder. The term "patient" includes human and veterinary subjects.

The term "muscarinic acetylcholine receptors" means G protein-coupled main end-receptors that are stimulated by acetylcholine released from several cell types including sensory neurons, keratinocytes, and postganglionic fibers in the parasympathetic nervous system, and function as signaling molecules that initiate signal cascades within cells in their immediate regions.

The term "muscarinic acetylcholine receptor antagonist" as used herein, means one or more extracted naturally occurring agents, purified naturally occurring agents, chemically synthesized agents, their salts, their derivatives, and their homologs, that reduce the activities of and/or function of muscarinic acetylcholine receptors that are found in neurons and other cells.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The term "therapeutically effective" means that the amount of the composition used is of sufficient quantity to ameliorate one or more causes or symptoms of a disease or disorder. Such amelioration only requires a reduction or alteration, not necessarily elimination. The "therapeutically effective amount" will vary depending on the compound, the disease and its severity and the age, weight, etc., of the subject to be treated.

As used herein, "pharmaceutical composition" includes any composition for: (i) topical administration, or (ii) transdermal administration or (iii) parenteral administration, or (iv) oral administration, of a muscarinic acetylcholine receptor antagonist to a subject in need of therapy for distal symmetrical polyneuropathy. Pharmaceutical compositions may include carriers, thickeners, diluents, buffers, preservatives, surface active agents and the like in addition to a muscarinic acetylcholine receptor antagonist(s). Pharmaceutical compositions may also include one or more active ingredients such as antimicrobial agents, anti-inflammatory agents, anaesthetics, and the like.

The term "unit dosage form" as used herein, refers to physically discrete units suitable as unitary dosages for human and animal subjects, each unit containing a predetermined quantity of muscarinic acetylcholine receptor antagonist(s) calculated in an amount sufficient to produce the desired effect in association with a pharmaceutically acceptable diluent, carrier or vehicle.

The term "carrier" means a compound, composition, substance, or structure that, when in combination with a muscarinic acetylcholine receptor antagonist or composition, aids or facilitates preparation, storage, administration, delivery, effectiveness, selectivity, or any other feature of the muscarinic acetylcholine receptor antagonist or composition for its intended use or purpose. For example, a carrier can be selected to minimize any degradation of the muscarinic acetylcholine receptor antagonists and to minimize any adverse side effects in the subject.

Suitable pharmaceutically acceptable carriers include essentially chemically inert and nontoxic pharmaceutical compositions that do not interfere with the effectiveness of the biological activity of the pharmaceutical composition. Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), dioleoylphosphatidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, oral administration requires enteric coatings to protect the muscarinic acetylcholine receptor antagonists from degradation within the gastrointestinal tract. In another example, the muscarinic acetylcholine receptor antagonists may be administered in a liposomal formulation to facilitate transport throughout a subject's vascular system and effect delivery across cell membranes to intracellular sites.

The term "excipient" herein means any substance, not itself a therapeutic agent, which may be used in a composition for delivery of muscarinic acetylcholine receptor antagonist(s) to a subject or alternatively combined with a muscarinic acetylcholine receptor antagonist (e.g., to create a pharmaceutical composition) to improve its handling or storage properties or to permit or facilitate formation of a dose unit of the composition (e.g., formation of a topical hydrogel which may then be optionally incorporated into a transdermal patch). Excipients include, by way of illustration and not limitation, binders, disintegrants, taste enhancers, solvents, thickening or gelling agents (and any neutralizing agents, if necessary), penetration enhancers, solubilizing agents, wetting agents, antioxidants, lubricants, emollients, substances added to mask or counteract a disagreeable odor, fragrances or taste, substances added to improve appearance or texture of the composition and substances used to form the pharmaceutical compositions. Any such excipients can be used in any dosage forms according to the present disclosure. The foregoing classes of excipients are not meant to be exhaustive but merely illustrative as a person of ordinary skill in the art would recognize that additional types and combinations of excipients could be used to achieve the desired goals for delivery of the muscarinic acetylcholine receptor antagonist(s).

Pirenzepine is a well-known medicant that is used for treating duodenal ulcers, stomach ulcers, and intestinal problems, either alone or in combination with antacids or other medicants such as ranitidine. Pirenzepine has been used to relieve cramps and/or spasms in the stomach, intestines and bladder. Additionally, pirenzepine can be used as a prophylactic to prevent nausea, vomiting and motion sickness. Pirenzepine belongs to the following drug categories: (a) anti-ulcer agents, (b) antimuscarinics, (c) antispasmodics, and (d) muscarinic antagonists.

The primary effects of pirenzepine are consequence of its binding to and modulation of the muscarinic acetylcholine receptor. The muscarinic acetylcholine receptor mediates various cellular responses, including inhibition of adenylate cyclase, breakdown of phosphoinositides and modulation of potassium channels through the action of G proteins. Current therapeutic uses of pirenzepine are based on orally administered compositions. Pirenzepine is absorbed from the gastro-digestive tract and after assimilation, modulates secretion of gastric acids, salivary secretions, the central nervous system, cardiovascular, ocular, and urinary functions. The effective dosages in orally administered pirenzepine compositions for these indications are in the range of about 50 to 300 mg/day, about 75 to 225 mg/day, about 100 to 150 mg/day.

The molecular formula for pirenzepine is $C_{19}H_{21}N_5O_2$ with a molecular weight of 351.402. Pirenzepine's IUPAC name is 11-[2-(4-methylpiperazin-1-yl)acetyl]-5H-pyrido[2,3-b][1,4]benzodiazepin-6-1. Pirenzepine is available as a HCl salt or hydrate.

We have surprisingly found that culturing excised adult and juvenile neurons from diabetic rats, in culture media comprising pirenzepine stimulates neurite outgrowth from the excised neurons. Additionally, we found that all of topical applications, subcutaneous injections, injections of pirenzepine to and into various skin targets in diabetic mice: (i) prevented deficits in motor nerve conduction velocity, (ii) prevented and reversed loss of intraepidermal nerve fibers, (iii) prevented loss of sub-epidermal nerve plexi, (iv) prevented tactile allodynia, and (v) prevented and reversed the development of thermal hypoalgesia. Furthermore, we have found that oral delivery of pirenzepine reversed sensory neuropathy.

In view of these remarkable results, we assessed other muscarinic acetylcholine receptor antagonists for their potential to reverse diabetes-associated loss of intraepidermal nerve fibers and thermal hypoalgesia. Muscarinic acetylcholine receptor antagonists are agents that reduce the activities and/or function of muscarinic acetylcholine receptors that are found in the plasma membranes of neurons and other cells. Muscarinic acetylcholine receptors are G protein-coupled main end-receptors that are stimulated by acetylcholine released from several cell types including sensory neurons, keratinocytes, and postganglionic fibers in the parasympathetic nervous system, and function as signaling molecules that initiate signal cascades within cells in their immediate regions. Well-known muscarinic acetylcholine receptor antagonists useful for treatment of maladies such as central nervous system malfunctioning, pulmonary diseases, and gastric ailments are exemplified by atropine, scopolamine, telenzepine, hyoscine, ipratropium tropicamide, cyclopentolate, glycopyrrolate, 4-diphenylacetoxy-1,1-dimethylpiperidinium, quinidine, orphenadrine, oxyphenonium, emepronium, procyclidine, propantheline, 4-fluorhexahydrosiladifenidol, octylonium, quinuclidinyl benzilate, tolterodine, benactyzine, biperiden, dicyclomine, benztropine, dexetimide, hexahydrosiladifenidol, among others.

Furthermore, in addition to pirenzepine, there are a number of selective antagonists of the type 1 muscarinic receptor (MIR) and other muscarinic receptor subtypes that are anticipated to exhibit beneficial activities similar to those demonstrated by pirenzepine on neuronal neurite outgrowth. Some of these compounds have much superior M1R selective activity. For example, telenzepine, an analog of pirenzepine with an altered tricyclic structure but an unmodified piperazine side chain, is 4 to 10 times more potent than pirenzepine. VU0255035, a thiadiazole derivative and is 75 times more selective to M1R relative to M2, M3, M4 and M5 receptors. Among the new generation of M1R antagonists, there are three promising centrally active M1R antagonists, PD150714, and 77-LH-28-1 and spirotramine. Listings of suitable muscarinic acetylcholine receptor antagonists suitable for incorporation into therapeutic compositions for distal symmetrical polyneuropathy and/or tactile allodynia are shown in Tables 1-4.

TABLE 1

Chemical classification of M1R antagonists and their representative structures.

| S. No | Structure | Name |
|---|---|---|
| | Muscarinic Toxin | |
| 1) | LTCVKSNSIWFPTSEDCPDGQNLCFKRWQYISPRMY—⌐<br>                               └—DFTRGCAATCPKAEYRDVINCCGTDKCNK | MT7(venom) |

TABLE 1-continued
Chemical classification of M1R antagonists and their representative structures.
| S. No | Structure | Name |
|---|---|---|
Tricyclic Benzodiazepinone Derivatives
2) 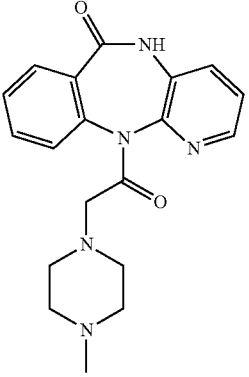 [SMILES: CN1CCN(CC(=O)N2c3ccccc3C(=O)Nc3cccnc32)CC1] Pirenzepine
3) 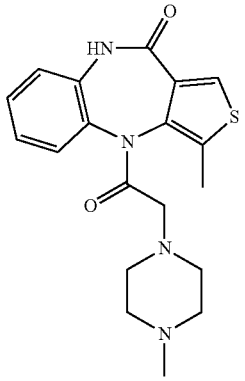 [SMILES: Cc1scc2c1N(C(=O)CN1CCN(C)CC1)c1ccccc1NC2=O] Telenzepine
1,4-Disubstituted Tetrahydropyridine Carboxylic Acids:
4) 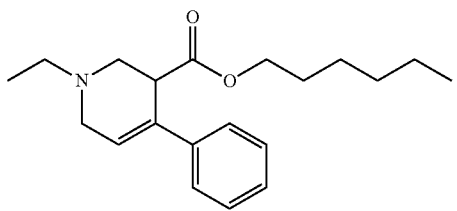 [SMILES: CCCCCCOC(=O)C1CN(CC)CC=C1c1ccccc1] PD150714
Trihexyphenidyl Analogs
5) 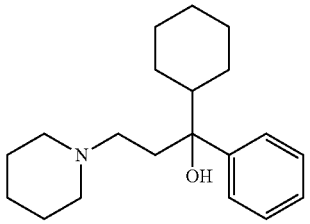 [SMILES: OC(CCN1CCCCC1)(c1ccccc1)C1CCCCC1] Trihexyphenidyl TABLE 1-continued Chemical classification of M1R antagonists and their representative structures.

| S. No | Structure | Name |
|---|---|---|
| 6) | 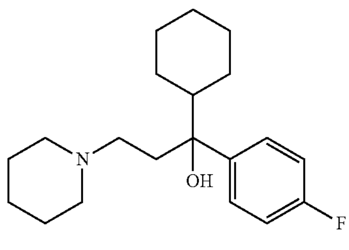 [SMILES: OC(CCN1CCCCC1)(c1ccc(F)cc1)C1CCCCC1] | p-fluorotrihexyphenidyl |

Thiadiazole Sulfonamide Derivatives

| 7) | | VU0255035 |

Hexocyclium and Sila-hexocyclium

| 8) | | O-methoxy-sila-hexocyclium |

Polymethylene Tetraamine or Spiro-4-DAMP(4-diphenyl-acetoxy-n-methylpiperidine)

| 9) | | Spirotramine |

N-(4-(4-ethylpiperazin-1-yl) phenyl amide analogues

| 10) | | |

TABLE 1-continued
Chemical classification of M1R antagonists and their representative structures.
| S. No | Structure | Name |
|---|---|---|
| | McN-A-343 Analogues | |
| 11) | 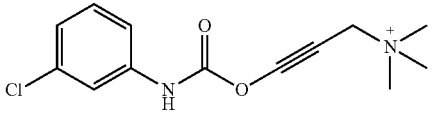 | McN-A-343 |
| 12) | 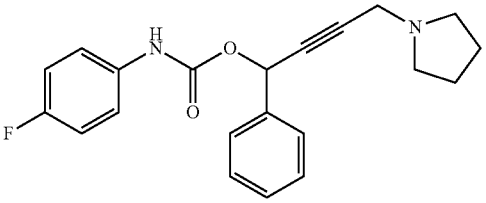 [SMILES: O=C(Nc1ccc(F)cc1)OC(C#CCN1CCCC1)c1ccccc1] | McN-A-343 analog |
| | Alkoxy-oxadiazolyltetrahydropyridines | |
| 13) | 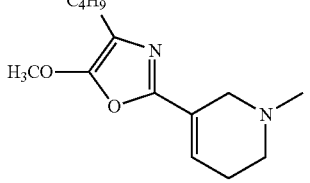 | MB-OXTP |
| | Caramiphen, aprophen and related derivatives | |
| 14) | 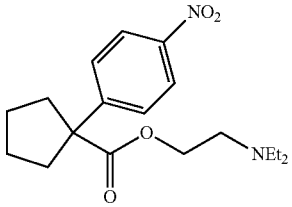 | Nitrocaramiphen |
| 15) | 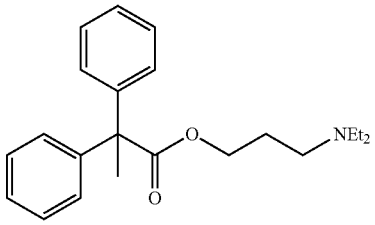 | Aprophen |
| | Miscellaneous | |
| 16) | 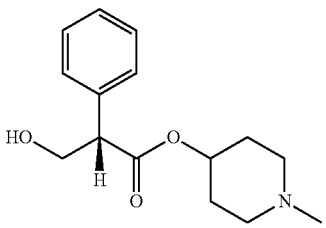 [SMILES: CN1CCC(OC(=O)[C@H](CO)c2ccccc2)CC1] | (−)-S-ET126 |

TABLE 1-continued

Chemical classification of M1R antagonists and their representative structures.

| S. No | Structure | Name |
|---|---|---|
| 17) | 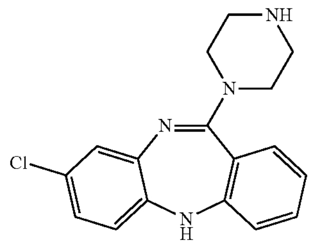 [SMILES: Clc1ccc2c(c1)N=C(N1CCNCC1)c1ccccc1N2] | N-desmethylclozapine |
| 18) | 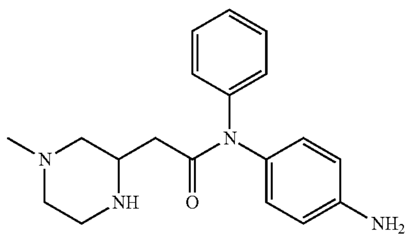 [SMILES: CN1CCNC(CC(=O)N(c2ccccc2)c2ccc(N)cc2)C1] | MDL74019DG |
| 19) | 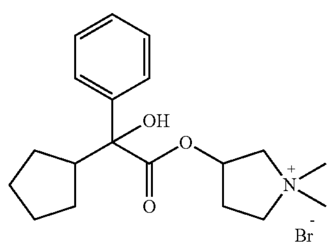 | Glycopyrronium bromide |
| 20) | 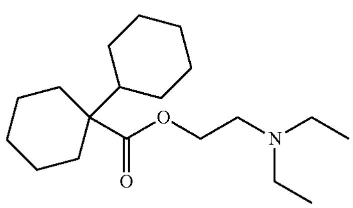 [SMILES: CCN(CC)CCOC(=O)C1(C2CCCCC2)CCCCC1] | Dicyclomine |

TABLE 2

M1R mixed antagonists, i.e. compounds that show antagonist effects at more than one subtype of muscarinic receptor, including M1.

| S. No | Structure | Name | Receptor Subtype |
|---|---|---|---|
| 1) | 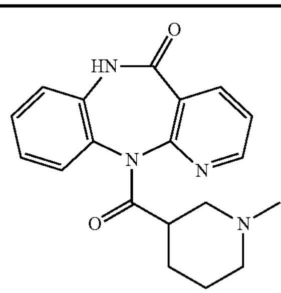 | Rispenzepine | M1/M3 antagonist |

TABLE 2-continued

M1R mixed antagonists, i.e. compounds that show antagonist effects at more than one subtype of muscarinic receptor, including M1.

| S. No | Structure | Name | Receptor Subtype |
|---|---|---|---|
| 2) | 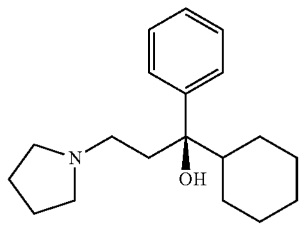 [SMILES: O[C@@](CCN1CCCC1)(c1ccccc1)C1CCCCC1] | R- Procyclidine | M1/M4 antagonist |
| 3) | 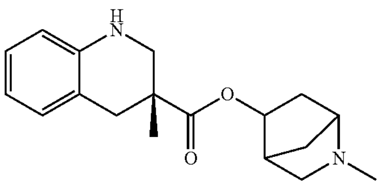 [SMILES: CN1CC2CC1CC2OC(=O)[C@@]1(C)CNc2ccccc2C1] | DAU 5750 | M1-M3 antagonist. |

TABLE 3

Selective non-M1 muscarinic antagonists (i.e. selective to M2, M3, M4 or M5)

| S. No. | Structure | Name | Receptor Subtype |
|---|---|---|---|
| 1) | 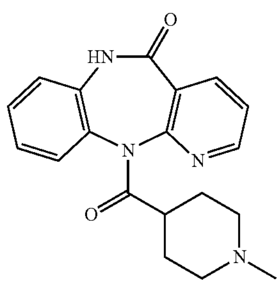 [SMILES: CN1CCC(C(=O)N2c3ccccc3NC(=O)c3cccnc32)CC1] | Nuvenzepine | M3 antagonist |
| 2) | 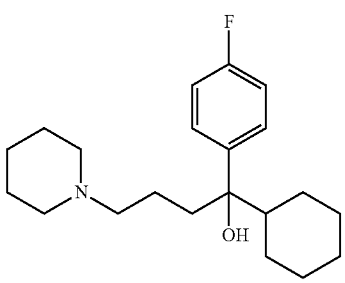 [SMILES: OC(CCCN1CCCCC1)(c1ccc(F)cc1)C1CCCCC1] | 4-Fluorohexahydro siladifenidol | M3 antagonist |
| 3) | 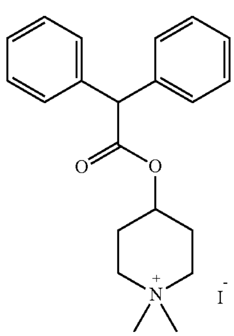 | 4-Diphenylacetoxy-N-methyl-piperidine methiodide | M3 antagonist |

TABLE 3-continued

Selective non-M1 muscarinic antagonists (i.e. selective to M2, M3, M4 or M5)

| S. No. | Structure | Name | Receptor Subtype |
|---|---|---|---|
| 4) | 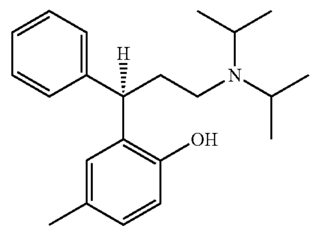 [SMILES: Cc1ccc(O)c([C@H](CCN(C(C)C)C(C)C)c2ccccc2)c1] | Tolterodine | M2/M3 antagonist |
| 5) | 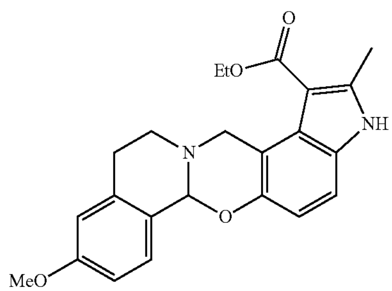 [SMILES: CCOC(=O)c1c(C)[nH]c2ccc3c(c12)CN1CCc2cc(OC)ccc2C1O3] | PD102807 | M4 antagonist |

TABLE 4

Non-selective muscarinic antagonists (scopolamine-based structures)

| S. No | Structure | Name | Clinical Indication | Route of administration |
|---|---|---|---|---|
| 1 | 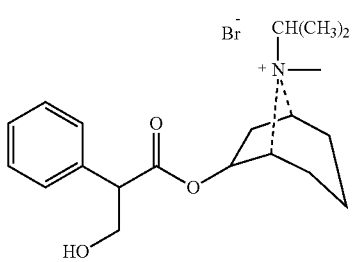 | Iptratropium bromide | COPD Acute asthma | Inhalation |
| 2 | 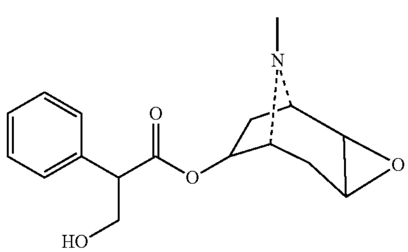 [SMILES: CN1[C@@H]2CC3OC3[C@@H]1CC2OC(=O)C(CO)c1ccccc1] | Scopolamine | Motion Sickness Intestinal cramping | Oral, IV, transdermal |

The above descriptions of the chemical structures in Tables 1 through 4 indicate that compounds exhibiting M1R selective activity require defined features and changes to the structures could make a M1R-selective antagonist to be M3R-selective or M2R selective, and vice versa. For example, compound 1 in Table 2 and compound 1 in Table 3 belong to the same class of drugs, but the change in the substitution pattern on the piperazine side chain determines the M1 vs M1/M3 selectivity. Thus, chemical compounds belonging to the above general chemical structures, but with structural variations, could still possess M1 selective antagonist activity thus enabling their use in diabetic symmetrical polyneuropathy. Accordingly, generic formulae can be designed that encompass the structural features for the antagonists, including those that are M1R selective and M1R-non-selective compounds. Suitable formulae are exemplified by Formula I and Formula II.

Formula I

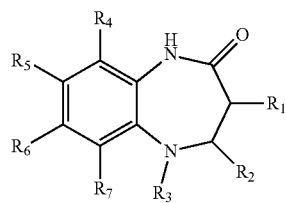

$R_1$ may be one of a 5-membered unsaturated ring, a 6-membered unsaturated ring, or a hetero atom-containing ring;

$R_2$ may be one of a 5-membered unsaturated ring, a 6-membered unsaturated ring, or a hetero atom-containing ring;

$R_3$ may be one of a H-piperidinyl group, a 2-piperidinyl group, a 3-piperidinyl, a 4-piperidinyl group, a 2-piperazinyl group, or a 3-piperazinyl group, linked via a methyl group or an ethyl group or a propyl group or a butyl group. The piperidinyl groups or piperazinyl groups may additionally be linked to methyl, trifluoromethyl or ethyl moieties.

$R_4$ may be a hydrogen ion or a chloride ion.

$R_5$ may be a hydrogen ion or a chloride ion.

$R_6$ may be a hydrogen ion or a chloride ion.

$R_7$ may be a hydrogen ion or a chloride ion.

Formula II

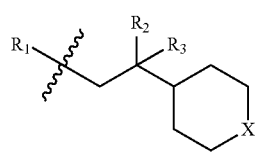

X may be a methyl group or a "NR" group i.e. a primary amine group, a secondary amine group, or a tertiary amine group.

$R_1$ may be

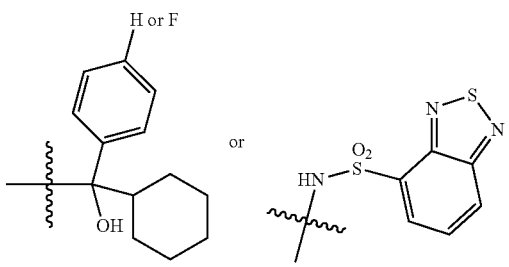

wherein

indicates the point of connection of $R_1$ with the upper structure in Formula II.

$R_2$ may be a hydroxyl ion or a hydrogen ion or a ketone.

$R_3$ may be a hydroxyl ion or a hydrogen ion or a ketone.

In one embodiment, the pharmaceutical compositions disclosed herein comprise a muscarinic acetylcholine receptor antagonist(s), in a total amount by weight of the composition of about 0.1% to about 95%. For example, the amount of a muscarinic acetylcholine receptor antagonist, by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

The pharmaceutical compositions of the present invention comprising a muscarinic acetylcholine receptor antagonist(s) may be formulated for topical administration or alternatively, for transdermal administration.

A pharmaceutical composition for topical administration may be provided as, for example, ointments, creams, suspensions, lotions, powders, solutions, pastes, gels, hydrogels, sprays, aerosols or oils. When formulated in an ointment, the active ingredient may be employed with either a paraffinic or a water-miscible ointment base. Alternatively, the active ingredient may be formulated in a cream with an oil-in-water base or a water-in-oil base.

A pharmaceutical composition for transdermal administration may be provided as, for example, a hydrogel comprising a muscarinic acetylcholine receptor antagonist(s) incorporated into an adhesive patch composition intended to remain in intimate contact with a subject's epidermis for a prolonged period of time. An exemplary adhesive patch composition can comprise a monolithic layer produced by mixing a muscarinic acetylcholine receptor antagonist(s) with a silicone-type adhesive or alternatively an acrylate-vinyl acetate adhesive in a solvent exemplified by methylene chloride, ethyl acetate, isopropyl myristate, and propylene glycol. The mixture would then be extruded onto a polyester-backing film to a uniform thickness of about 100 microns or greater with a precision wet-film applicator. The solvent is allowed to evaporate in a drying oven and the resulting "patch" is trimmed to the appropriate size.

The pharmaceutical composition for topical administration or alternatively for transdermal administration of a muscarinic acetylcholine receptor antagonist(s) may additionally incorporate a penetration enhancer and/or a thickening agent or gelling agent and/or an emollient and/or an antioxidant and/or an antimicrobial preservative and/or an emulsifying agent and/or a water miscible solvent and/or an alcohol and/or water.

According to one aspect, the pharmaceutical composition for topical administration or transdermal administration of a muscarinic acetylcholine receptor antagonist(s) may comprise one or more penetration enhancing agent or co-solvent for transdermal or topical delivery. A penetration enhancer is an excipient that aids in the diffusion of the active through the stratum corneum. Many penetration enhancers also function as co-solvents which are thought to increase the thermodynamic activity or solubility of the muscarinic acetylcholine receptor antagonist in the composition. Penetration enhancers are also known as accelerants, adjuvants or sorption promoters. A suitable penetration enhancer for use in the pharmaceutical compositions and methods described herein should: (i) be highly potent, with a specific mechanism of action; (ii) exhibit a rapid onset upon administration; (iii) have a predictable duration of action; (iv) have only non-permanent or reversible effects on the skin; (v) be chemically stable; (vi) have no or minimal pharmacological effects; (vii) be physically and chemically compatible with other composition components; (viii) be odorless; (ix) be colorless; (x) be hypoallergenic; (xi) be non-irritating; (xii) be non-phototoxic; (xiii) be non-comedogenic; (xiv) have a solubility parameter approximating that of the skin (10.5 cal/cm3); (xv) be readily available; (xvi) be inexpensive; and (xvii) be able to formulated in pharmaceutical compositions for topical or transdermal delivery of an active pharmaceutical agent.

Several classes of chemical compounds, with various mechanisms of action, can be used as penetration enhancers. Set forth below are non-limiting examples of penetration enhancing agents, many of which are also suitable co-solvents. Sulfoxides, such as dimethylsulfoxide and decylmethylsulfoxide can be used as penetration enhancing agents. Dimethylsulfoxide enhances penetration in part by increasing lipid fluidity and promoting drug partitioning. In contrast, decylmethylsulfoxide enhances penetration by reacting with proteins in the skin that change the conformation of the proteins, which results in the creation of aqueous channels.

Another class of a penetration enhancers are alkanones, such as N-heptane, N-octane, N-nonane, N-decane, N-undecane, N-dodecane, N-tridecane, N-tetradecane and N-hexadecane. Alkanones are thought to enhance the penetration of an active agent by altering the stratum corneum. A further class of penetration enhancers are alkanol alcohols, such as ethanol, propanol, butanol, 2-butanol, pentanol, 2-pentanol, hexanol, octanol, nonanol, decanol and benzyl alcohol. Low molecular weight alkanol alcohols, i.e., those with 6 or less carbons, may enhance penetration in part by acting as solubilizing agents, while more hydrophobic alcohols may increase diffusion by extracting lipids from the stratum corneum. A further class of penetration enhancers are fatty alcohols, such as oleyl alcohol, caprylic alcohol, decyl alcohol, lauryl alcohol, 2-lauryl alcohol, myristyl alcohol, cetyl alcohol, stearyl alcohol, oleyl alcohol, linoleyl alcohol and linolenyl alcohol. Polyols, including propylene glycol, polyethylene glycol, ethylene glycol, diethylene glycol, triethylene glycol, dipropylene glycol, glycerol, propanediol, butanediol, pentanediol, hexanetriol, propylene glycol monolaurate and diethylene glycol monomethyl ether (transcutol), can also enhance penetration. Some polyols, such as propylene glycol, may function as a penetration enhancer by solvating alpha-keratin and occupying hydrogen bonding sites, thereby reducing the amount of active-tissue binding.

Another class of penetration enhancers are amides, including urea, dimethylacetamide, diethyltoluamide, dimethylformamide, dimethyloctanamide, dimethyldecanamide and biodegradable cyclic urea (e.g., 1-alkyl-4-imidazolin-2-one). Amides have various mechanisms of enhancing penetration. For example, some amides, such as urea increase the hydration of the stratum corneum, act as a keratolytic and create hydrophilic diffusion channels. In contrast, other amides, such as dimethylacetamide and dimethylformamide, increase the partition to keratin at low concentrations, while increasing lipid fluidity and disrupting lipid packaging at higher concentrations. Another class of penetration enhancing agents are pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-methyl-pyrrolidone, N-cyclohexylpyrrolidone, N-dimethylaminopropyl-pyrrolidone, N-cocoalkylpyrrolidone and N-tallowalkylpyrrolidone, as well as biodegradable pyrrolidone derivatives, including fatty acid esters of N-(2-hydroxyethyl)-2-pyrrolidone. In part, pyrrolidone derivatives enhance penetration through interactions with the keratin in the stratum corneum and lipids in the skin structure. An additional class of penetration enhancers are cyclic amides, including 1-dodecylazacycloheptane-2-one also known as Azone® (Azone is a registered trademark of Echo Therapeutics Inc., Franklin, MA, USA), 1-geranylazacycloheptan-2-one, 1-farnesylazacycloheptan-2-one, 1-geranylgeranylazacycloheptan-2-one, 1-(3,7-dimethyl octyl)-azacycloheptan-2-one, 1-(3,7,11-trimethyldodecyl)azacycloheptan-2-one, 1-geranylazacyclohexane-2-one, 1-geranylazacyclopentan-2,5-dione and 1-farnesylazacyclopentan-2-one. Cyclic amides, such as Azone®, enhance the penetration of active agents in part by affecting the stratum corneum's lipid structure, increasing partitioning and increasing membrane fluidity. Additional classes of penetration enhancers include diethanolamine, triethanolamine and hexamethylenelauramide and its derivatives.

Additional penetration enhancers include linear fatty acids, such as octanoic acid, linoleic acid, valeric acid, heptanoic acid, pelargonic acid, caproic acid, capric acid, lauric acid, myristic acid, stearic acid, oleic acid and caprylic acid. Linear fatty acids enhance penetration in part via selective perturbation of the intercellular lipid bilayers. In addition, some linear fatty acids, such as oleic acid, enhance penetration by decreasing the phase transition temperatures of the lipid, thereby increasing motional freedom or fluidity of the lipids. Branched fatty acids, including isovaleric acid, neopentanoic acid, neoheptanoic acid, nonanoic acid, trimethyl hexanoic acid, neodecanoic acid and isostearic acid, are a further class of penetration enhancers. An additional class of penetration enhancers are aliphatic fatty acid esters, such as ethyl oleate, isopropyl n-butyrate, isopropyl n-hexanoate, isopropyl n-decanoate, isopropyl myristate ("IPM"), isopropyl palmitate and octyldodecyl myristate. Aliphatic fatty acid esters enhance penetration by increasing diffusivity in the stratum corneum and/or the partition coefficient. In addition, certain aliphatic fatty acid esters, such as IPM, enhance penetration by directly acting on the stratum corneum and permeating into the liposome bilayers thereby increasing fluidity. Alkyl fatty acid esters, such as ethyl acetate, butyl acetate, methyl acetate, methyl valerate, methyl propionate, diethyl sebacate, ethyl oleate, butyl stearate and methyl laurate, can act as penetration enhancers. Alkyl fatty acid esters enhance penetration in part by increasing the lipid fluidity.

An additional class of penetration enhancers are anionic surfactants, including sodium laurate, sodium lauryl sulfate and sodium octyl sulfate. Anionic surfactants enhance penetration of active agents by altering the barrier function of the stratum corneum and allowing removal of water-soluble agents that normally act as plasticizers. A further class of penetration enhancers are cationic surfactants, such as cetyltrimethylammonium bromide, tetradecyltrimethylammonium, octyltrimethyl ammonium bromide, benzalkonium chloride, octadecyltrimethylammonium chloride, cetylpyridinium chloride, dodecyltrimethylammonium chloride and hexadecyltrimethylammonium chloride. Cationic surfactants enhance penetration by adsorbing at, and interacting with, interfaces of biological membranes, resulting in skin damage. A further class of penetration enhancers are zwitterionic surfactants, such as hexadecyl trimethyl ammoniopropane sulfonate, oleyl betaine, cocamidopropyl hydroxysultaine and cocamidopropyl betaine. Nonionic surfactants exemplified by Poloxamer 231, Poloxamer 182, Poloxamer 184, Polysorbate 20, Polysorbate 60, Brij® 30, Brij® 93, Brij® 96, Brij® 99 (Brij is a registered trademark of Uniqema Americas LLC, Wilmington, DE, USA), Span® 20, Span® 40, Span® 60, Span® 80, Span® 85 (Span is a registered trademark of Uniqema Americas LLC, Wilmington, DE, USA), Tween® 20, Tween® 40, Tween® 60, Tween® 80 (Tween is a registered trademark of Uniqema Americas LLC, Wilmington, DE, USA), Myrj 45, Myrj 51, Myrj 52, and Miglyol® 840 (Miglyol is a registered trademark of Sasol Germany GMBH Corp, Hamburg, Fed. Rep. Germany), and the like. Nonionic surfactants enhance penetration in part by emulsifying the sebum and enhancing the thermodynamic activity or solubility of the active.

Another class of penetration enhancer increase the thermodynamic activity or solubility of the active, which include, but are not limited to, n-octanol, sodium oleate, D-limonene, monoolein, cineol, oleyl oleate, and isopropyl myristate.

Other penetration enhancers are bile salts, such as sodium cholate, sodium salts of taurocholic acid, glycolic acids and deoxycholic acids. Lecithin also has been found to have penetration enhancing characteristics. An additional class of penetration enhancers are terpenes, which include hydrocarbons, such as d-limonene, alpha-pinene and beta-carene; alcohols, such as, alpha-terpineol, terpinen-4-ol and carvol; ketones, such as carvone, pulegone, piperitone and menthone; oxides, such as cyclohexene oxide, limonene oxide, alpha-pinene oxide, cyclopentene oxide and 1,8-cineole; and oils such as ylang ylang, anise, *Chenopodium* and *eucalyptus*. Terpenes enhance penetration in part by disrupting the intercellular lipid bilayer to increase diffusivity of the active and opening polar pathways within and across the stratum corneum. Organic acids, such as salicylic acid and salicylates (including their methyl, ethyl and propyl glycol derivatives), citric acid and succinic acid, are penetration enhancers. Another class of penetration enhancers are cyclodextrins, including 2-hydroxypropyl-beta-cyclodextrin and 2,6-dimethyl-beta-cyclodextrin. Cyclodextrins enhance the permeation of active agents by forming inclusion complexes with lipophilic actives and increasing their solubility in aqueous solutions.

The penetration enhancing agent(s) and/or co-solvent(s) is/are present in the pharmaceutical composition for topical administration or transdermal administration of a muscarinic acetylcholine receptor antagonist(s) in an amount sufficient to provide the desired level of drug transport through the stratum corneum and epidermis or to increase the thermodynamic activity or solubility of the acetylcholine receptor antagonist(s). The one or more pharmaceutically acceptable penetration enhancer and/or co-solvent may be present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, about 40%, about 41%, about 42%, about 43%, about 44%, about 45%, about 46%, about 4'7%, about 48%, about 49%, about 50%, about 51%, about 52%, about 53%, about 54%, about 55%, about 56%, about 5'7%, about 58%, about 59%, about 60%, about 61%, about 62%, about 63%, about 64%, about 65%, about 66%, about 6'7%, about 68%, about 69%, about 70%, about 71%, about 72%, about 73%, about 74%, about 75%, about 76%, about 7'7%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

According to another aspect, the pharmaceutical composition for topical administration or for transdermal application of a muscarinic acetylcholine receptor antagonist(s) may comprise a thickening or gelling agent suitable for use in the compositions and methods described herein to increase the viscosity of the composition. Suitable agents (also known as gelling agents) are exemplified neutralized anionic polymers or neutralized carbomers, such as polyacrylic acid, carboxypolymethylene, carboxymethylcellulose and the like, including derivatives of Ultrez 10, Carbopol® polymers, such as Carbopol® Carbopol® 940, Carbopol® 941, Carbopol® 954, Carbopol® 980, Carbopol® 981, Carbopol® ETD 2001, Carbopol® EZ-2 and Carbopol® EZ-3. (Carbopol is a registered trademark of Lubrizol Advanced Materials Inc., Cleveland, OH, USA). As used herein, a "neutralized carbomer" is a synthetic, high molecular weight polymer, composed primarily of a neutralized polyacrylic acid. Further, when a base is added to neutralize a carbomer solution, the viscosity of the solution increases. Also suitable are other known polymeric thickening agents, such as Pemulen® polymeric emulsifiers, Noveon® polycarbophils (Pemulen and Noveon are registered trademarks of Lubrizol Advanced Materials Inc.), and Klucel® (Klucel is a registered trademark of Hercules Inc., Wilmington, DE, USA). Additional thickening agents, enhancers and adjuvants may generally be found in Remington's The Science and Practice of Pharmacy as well as the Handbook of Pharmaceutical Excipients, Arthur H. Kibbe ed. 2000. Alternatively, the pharmaceutical composition for topical administration or for transdermal application of a muscarinic acetylcholine receptor antagonist(s) may comprise an anionic polymer thickening agent precursor, such as a carbomer, which has been combined with a neutralizer in an amount sufficient to form a gel or gel-like composition with a viscosity greater than 1000 cps as measured by a Brookfield RV DVII+ Viscometer with spindle CPE-52, torque greater than 10% and the temperature maintained at 25° C. Alternatively, the anionic polymer thickening agent precursor may be combined with a neutralizer selected from the group consisting of: sodium hydroxide, ammonium hydroxide, potassium hydroxide, arginine, aminomethyl propanol, tetrahydroxypropyl ethylenediamine, triethanolamine ("TEA"), tromethamine, PEG-15 cocamine, diisopropanolamine, and triisopropanolamine, or combinations thereof in an amount sufficient to neutralize the anionic polymer thickening agent precursor to form a gel or gel-like composition in the course of forming the composition. The thickening agents or gelling agents are present in an amount sufficient to provide the desired rheological properties of the composition, which include having a sufficient viscosity for forming a gel or gel-like composition that can be applied to the skin of a mammal. The thickening agent or gelling agent is present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 11%, about 11.5%, about 12%, about 12.5%, about 13%, about 13.5%, about 14%, about 14.5% or about 15%.

According to another aspect, the pharmaceutical composition for topical administration or for transdermal application of a muscarinic acetylcholine receptor antagonist(s) may comprise an emollient. Suitable emollients are exemplified by mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, *althea officinalis* extract, arachidyl alcohol, argobase EUC, butylene glycol, dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soyabean, octyl palmitate, caprylic/capric triglyceride and glyceryl cocoate. An emollient, if present, is present in the compositions described herein in an amount by weight of the composition of about 1% to about 30%, about 3% to about 25%, or about 5% to about 15%. Illustratively, one or more emollients are present in a total amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight.

According to another aspect, the pharmaceutical composition for topical administration or for transdermal application of a muscarinic acetylcholine receptor antagonist(s) may comprise an antioxidant. Suitable antioxidants are exemplified by citric acid, butylated hydroxytoluene (BHT), ascorbic acid, glutathione, retinol, α-tocopherol, β-carotene, α-carotene, ubiquinone, butylated hydroxyanisole, ethylenediaminetetraacetic acid, selenium, zinc, lignan, uric acid, lipoic acid, and N-acetylcysteine. An antioxidant, if present, is present in the compositions described herein in a total amount selected from the range of about 0.025% to about 1.0% by weight.

According to another aspect, the pharmaceutical composition for topical administration or for transdermal application of a muscarinic acetylcholine receptor antagonist(s) may comprise an antimicrobial preservative. Illustrative anti-microbial preservatives include acids, including but not limited to, benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate or thimerosal. The anti-microbial preservative, if present, is present in an amount by weight of the composition of about 0.1% to about 5%, about 0.2% to about 3%, or about 0.3% to about 2%, for example about 0.2%, about 0.4%, about 0.6%, about 0.8%, about 1%, about 1.2%, about 1.4%, about 1.6%, about 1.8%, about 2%, about 2.2%, about 2.4%, about 2.6%, about 2.8%, about 3.0%, about 3.2%, about 3.4%, about 3.6%, about 3.8%, about 4%, about 4.2%, about 4.4%, about 4.6%, about 4.8%, or about 5%.

According to another aspect, the pharmaceutical composition for topical administration or for transdermal application of a muscarinic acetylcholine receptor antagonist(s) may comprise one or more emulsifying agents. The term "emulsifying agent" refers to an agent capable of lowering surface tension between a non-polar and polar phase and includes self-emulsifying agents. Suitable emulsifying agents can come from any class of pharmaceutically acceptable emulsifying agents exemplified by carbohydrates, proteins, high molecular weight alcohols, wetting agents, waxes and finely divided solids. The optional emulsifying agent, if present, is present in a composition in a total amount of about 1% to about 25%, about 1% to about 20%, or about 1% to about 15% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

According to another aspect, the pharmaceutical composition for topical administration or for transdermal application of a muscarinic acetylcholine receptor antagonist(s) may comprise a water miscible solvent exemplified by propylene glycol. A suitable water miscible solvent refers to any solvent that is acceptable for use in a pharmaceutical composition and is miscible with water. If present, the water miscible solvent is present in a composition in a total amount of about 1% to about 95%, about 2% to about 75%, about 3% to about 50%, about 4% to about 40%, or about 5% to about 25% by weight of the composition.

According to another aspect, the pharmaceutical composition for topical administration or for transdermal application of a muscarinic acetylcholine receptor antagonist(s) may comprise one or more alcohols. In a further embodiment, the alcohol is a lower alcohol. As used herein, the term "lower alcohol," alone or in combination, means a straight-chain or branched-chain alcohol moiety containing one to about six carbon atoms. In one embodiment, the lower alcohol contains one to about four carbon atoms, and in another embodiment the lower alcohol contains two or three carbon atoms. Examples of such alcohol moieties include methanol, ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP or in any common form including in combination with various amounts of water. If present, the alcohol is present in an amount sufficient to form a composition which is suitable for contact with a mammal. For example, in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%.

According to another aspect, the pharmaceutical composition for topical administration or for transdermal application of a muscarinic acetylcholine receptor antagonist(s) may comprise water separately in a quantity or amount sufficient to achieve the desired weight of the pharmaceutical composition.

The muscarinic acetylcholine receptor antagonist(s) comprises about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 55%, about 60%, about 65%, about 70%, about 75%, about 80%, about 85%, about 90% or about 95% by weight of the pharmaceutical composition for topical application or for transdermal application.

Another embodiment pertains to pharmaceutical compositions comprising a muscarinic acetylcholine receptor antagonist(s) formulated for parenteral administration by injection. The injectable pharmaceutical compositions of the present invention comprise a suitable carrier solution exemplified by sterile water, saline, and buffered solutions at physiological pH. Suitable buffered solutions are exemplified by Ringer's dextrose solution and Ringer's lactated solutions. The carrier solution may comprise in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, ab out 1.5%, about 1.6%, about 1.7%, about 1.8%, about 1.9%, ab out 2.0%, about 2.1%, ab out 2.2%, about 2.3%, about 2.4%, about 2.5%, about 2.6%, ab out 2.7%, about 2.8%, ab out 2.9%, about 3.0%, about 3.1%, about 3.2%, about 3.3%, about 3.4%, about 3.5%, ab out 3.6%, about 3.7%, about 3.8%, about 3.9%, about 4.0%, ab out 4.1%, about 4.2%, ab out 4.3%, about 4.4%, about 4.5%, about 4.6%, about 4.7%, ab out 4.8%, about 4.9%, about 5.0%, about 5.1%, about 5.2%, about 5.3%, 5.4%, ab out 5.5%, about 5.6%, ab out 5.7%, about 5.8%, about 5.9%, about 6.0%, about 6.1%, ab out 6.2%, about 6.3%, ab out 6.4%, about 6.5%, about 6.6%, about 6.7%, about 6.8%, ab out 6.9%, about 7.0%, ab out 7.1%, about 7.2%, about 7.3%, about 7.4%, about 7.5%, ab out 7.6%, about 7.7%, about 7.8%, about 7.9%, about 8.0%, about 8.1%, about 8.2%, about 8.3%, about 8.4%, ab out 8.5%, about 8.6%, about 8.7%, about 8.8%, about 8.9%, ab out 9.0%, about 9.1%, about 9.2%, about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

According to one aspect, the injectable pharmaceutical compositions may additionally incorporate one or more non-aqueous solvents exemplified by propylene glycol, polyethylene glycol, vegetable oils such as olive oil, and injectable organic esters exemplified by ethyl oleate.

According to another aspect, the injectable pharmaceutical compositions may additionally incorporate one or more of antimicrobials, anti-oxidants, chelating agents and the like.

The injectable pharmaceutical compositions may be presented in unit-dose or multi-dose containers exemplified by sealed ampules and vials. The injectable pharmaceutical compositions may be stored in a freeze-dried (lyophilized) condition requiring the addition of a sterile liquid carrier, e.g., sterile saline solution for injections, immediately prior to use.

Another embodiment pertains to pharmaceutical compositions comprising a muscarinic acetylcholine receptor antagonist(s) formulated for oral administration. The oral pharmaceutical compositions may be provided as capsules or tablets; as powders or granules; as solutions, syrups or suspensions (in aqueous or non-aqueous liquids). Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols, etc. Solutions and syrups may comprise, for example, water, polyols and sugars. The muscarinic acetylcholine receptor antagonist(s) may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

The pharmaceutical compositions described herein are used in a "pharmacologically effective amount." A "pharmacologically effective amount" is the amount of the muscarinic acetylcholine receptor antagonist(s) in the composition which is sufficient to deliver a therapeutic amount of the active agent during the dosing interval in which the pharmaceutical composition is administered. Accordingly, the amount of the pharmaceutical composition administered to deliver a therapeutically effective amount of the muscarinic acetylcholine receptor antagonist(s) is about 0.01 g, about 0.05 g, about 0.1 g, about 0.2 g, about 0.3 g, about 0.4 g, about 0.5 g, about 0.6 g, about 0.7 g, about 0.8 g, about 0.9 g, about 1 g, about 1.1 g, about 1.2 g, about 1.3 g, about 1.4 g, about 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, about 5 g, about 5.1 g, about 5.2 g, about 5.3 g, about 5.4 g, about 5.5 g, about 5.6 g, about 5.7 g, about 5.8 g, about 5.9 g, about 6 g, about 6.1 g, about 6.2 g, about 6.3 g, about 6.4 g, about 6.5 g, about 6.6 g, about 6.7 g, about 6.8 g, about 6.9 g, about 7 g, about 7.1 g, about 7.2 g, about 7.3 g, about 7.4 g, about 7.5 g, about 7.6 g, about 7.7 g, about 7.8 g, about 7.9 g, about 8 g, about 8.1 g, about 8.2 g, about 8.3 g, about 8.4 g, about 8.5 g, about 8.6 g, about 8.7 g, about 8.8 g, about 8.9 g, about 9 g, about 9.1 g, about 9.2 g, about 9.3 g, about 9.4 g, about 9.5 g, about 9.6 g, about 9.7 g, about 9.8 g, about 9.9 g or about 10 g.

The following examples are provided to more fully describe the invention and are presented for non-limiting illustrative purposes.

EXAMPLES

Figure 1:
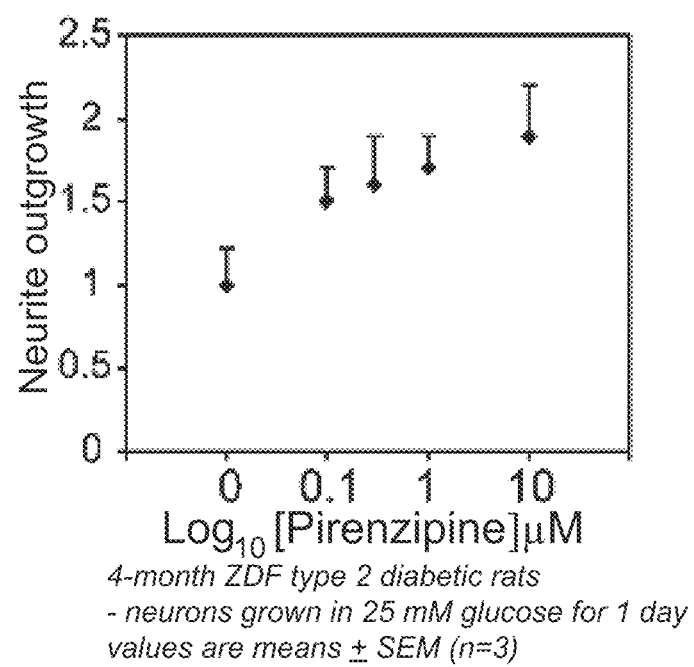
FIG. 1 is a chart showing the effects of pirenzepine, a specific muscarinic acetylcholine type 1 receptor (M1R)

Example 1: Effects of Pirenzepine on Outgrowth of Neurites from Excised Neurons in a Type 2 Diabetes Rat Model Sensory neurons from cervical, thoracic and lumbar DRG of a 3-4 month old adult male ZDF diabetic rat (model of type 2 diabetes) were isolated and dissociated using a method based on the teachings of Fernyhough et al. (1993, Brain Res. 607:117-124), Gardiner et al. (2005, Mol. Cell Neurosci. 28:229-240), and Huang et al. (2003, Diabetes 52:2129-2136). Briefly, DRG were removed from all spinal levels, their roots trimmed, and then the cells were chemically dissociated in 0.125% collagenase (Worthington Biochemical Corp., Lakewood, NJ, USA) in F12 nutrient medium (Invitrogen Canada Inc., Burlington, ON, Canada) for 1.5 h at 37° C. The ganglia were then mechanically dissociated by treatment with 0.05% trypsin (Worthington Biochemical Corp.) in F12 nutrient medium, followed by trituration with a glass pipette. The resulting cell suspension was then centrifuged at 600 rpm for 5 min through a cushion of 15% bovine serum albumin (BSA; Sigma-Aldrich Canada Ltd., Oakville, ON, Canada); this procedure eliminated much of the cellular debris and resulted in a neuronally enriched pellet of dissociated neurons. The neuron cells were plated onto poly-L-ornithine-laminin-coated NUNC 48-well or 96-well plastic dishes with optically clear glass bottoms in serum-free and insulin-free F12 medium in the presence of modified N2 additives (containing no insulin) at 37° C. in a 95% air/5% $CO_2$ humidified incubator. All cultures were exposed to the following additional conditions: 10 mM D-glucose, 0.1 nM insulin, 0.3 ng/ml NGF, 1 ng/ml NT-3 and 5 ng/ml GDNF (all obtained from Sigma-Aldrich Canada Ltd.). Upon plating, the neurons were immediately treated with pirenzepine-HCl dosages ranging from 0 to 10 µM. Neurite outgrowth was then assessed at 24 hr as previously described by Fernyhough et al. (1993) and Gardiner et al. (2005). The data in FIG. 1 show that increasing dosages of 0.1, 0.5, 1.0 and 10.0 µM of pirenzepine-HCl progressively increased neurite outgrowth from the excised neurons from a diabetes type 2 model.

Example 2: Effects of Selected Muscarinic Acetylcholine Receptor Antagonists on the Outgrowth of Neurites from Excised Neurons from a Normal Rat Sensory neurons from cervical, thoracic and lumbar DRG of a 3-4 month old non-diabetic adult male Sprague Dawley rat were isolated and dissociated using the method described in Example 1. The excised and dissociated neuron cells were plated onto poly-L-ornithine-laminin-coated NUNC 48-well or 96-well plastic dishes with optically clear glass bottoms in serum-free and insulin-free F12 medium in the presence of modified N2 additives (containing no insulin) at 37° C. in a 95% air/5% $CO_2$ humidified incubator. All cultures were exposed to the following additional conditions: 10 mM D-glucose, 0.1 nM insulin, 0.3 ng/ml NGF, 1 ng/ml NT-3 and 5 ng/ml GDNF (all obtained from Sigma-Aldrich Canada Ltd.). Upon plating, the neurons were exposed to these conditions and immediately treated with one of the following three muscarinic acetylcholine receptor antagonists: (A) pirenzepine-HCl dosages ranging from 0 to 10 μM, (B) telenzepine-2HCl dosages ranging from 0 to 10 μM, and (C) atropine dosages ranging from 0 to 1.0 μM. Neurite outgrowth was then assessed at 24 hr. The data in FIG. 2(A) show that the lowest pirenzepine dosage of 0.01 μM more than tripled neurite outgrowth from the excised neurons from a non-diabetic model, and that increasing pirenzepine dosages of 0.1, 1.0, and 10.0 μM did not further increase neurite outgrowth rates. The data in FIG. 2(B) show that the lowest telenzepine dosage of 0.01 μM more than doubled neurite outgrowth from the excised neurons from a non-diabetic model, and that the 0.1 μM and the 10.0 μM dosages tripled the neurite outgrowth rates. The data in FIG. 2(C) show that the lowest atropine dosage of 0.01 μM more than tripled neurite outgrowth from the excised neurons from a non-diabetic model, and that the 0.1 μM and the 10.0 μM dosages did not further increase neurite outgrowth rates.

Example 3: Effects of Low Concentrations of Two Selective M1R Antagonists on the Outgrowth of Neurites from Excised Neurons in a Normal Rat Sensory neurons from cervical, thoracic and lumbar DRG of an adult 3-4 month old male Sprague Dawley rat were isolated and dissociated using the method described in Example 1, and then were cultured for 24 h in serum-free and insulin-free F12 medium in the presence of modified N2 additives. Upon plating, the neurons were immediately treated with either: (A) pirenzepine-HCl dosages ranging from 0 to 0.1 μM (solid diamonds), or (B) a novel antimuscarinic agent code-named "VU255035" (solid squares). VU0255035 [N-(3-oxo-3-(4-(pyridine-4-yl)piperazin-1-yl) propyl)-benzo[c][1,2,5]thiadiazole-4 sulfonamide] is a novel M1R specific antagonist (Sheffler et al., 2009, Molecular Pharmacology 76: 356-368). Equilibrium radioligand binding and functional studies demonstrate a greater than 75-fold selectivity of VU0255035 for M1R relative to M(2)-M(5). Molecular pharmacology and mutagenesis studies indicate that VU0255035 is a competitive orthosteric antagonist of M1R. VU0255035 has excellent blood brain barrier penetration in vivo in mice. Neurite outgrowth was then assessed after a culture period of 24 hr.

Total neurite lengths (i.e., the sum of the length of all neurites produced by an individual neuron) were assessed using an immunostaining method. A Greiner Bio-One μClear 96 well tissue culture plate (Greiner Bio-One North America Inc., Munroe, NC, US) with a thin optically clear plastic growing surface to optimize neurite outgrowth conditions. Four images were captured per well and the replicate well frequency was set to n=6. The neuronal marker β-tubulin III (Sigma-Aldrich Canada Ltd.) was applied to formalin fixed cells. The marker was tagged with the fluorescent conjugate Alexa Fluor 488 (Invitrogen Canada Ltd.). Fluorescent images were collected using an Olympus IX71 inverted microscope with a 20×/0.45 PH1 LUCPLANFLN objective that was suitable for resolving images on plastic surfaces. This system was equipped with a Xenon short arc lamp and a Delta Ram X monochromator (Photon Technology International, Birmingham, NJ, US) to provide a reliable excitation wavelength. Captured image fluorescence was thereafter converted to a grayscale 8-bit image to quantify total pixel volume. Specifically the raw TIFF image was opened using the public domain NIH sponsored image processing software Image J. The image was first inverted to create a black target image against a white background and then background pixel volume minimized by threshold adjustment. Subsequent images were standardized against the adjusted threshold value for continuity. Total pixel volume of the neuron specific cell bodies and neurites were quantified. Pixel volume of the cell bodies were removed to yield a net pixel volume attributed to neurites. The net pixel volume was normalized against the number of neuronal cells per quantified field. The data in FIG. 3 show that: (A) pirenzepine concentrations of 0.003 μM and greater significantly increased total neurite outgrowth in neurons isolated from a diabetic rat, and (B) VU255035 concentrations of 0.03 μM and greater significantly increased total neurite outgrowth in neurons isolated from a diabetic rat.

Example 4: Responses of Sensory Neuron Cultures Derived from M1R Knockout Mice, to Pirenzepine Treatments Sensory neurons from cervical, thoracic and lumbar DRG sensory neurons were isolated from (A) wildtype mice (on a 129S6×CF1 background), and from (B) M1R knockout mice (from Taconic, Hudson, NY and mediated through a collaboration with the Laboratory of Bioorganic Chemistry, NIH-NIDDK, Bethesda, MD) generally following the method outlined in Example 1. The muscarinic acetylcholine receptor $M_1$ (M1R), also known as the cholinergic receptor, has been inactivated in M1R knockout mice and therefore, administration of muscarinic acetylcholine receptor antagonists that specifically inactivate the $M_1$ muscarinic acetylcholine receptor will not be physiologically effective in M1R knockout mice. The isolated DRG sensory neurons from the wildtype mice and the M1R knockout mice were separately cultured for 24 hr in a range of neurotrophic growth factor concentrations (NTs) plus 1 μM pirenzepine. The low dose (LD) cocktail of growth factors induced a significantly higher level of neurite outgrowth in cultures from M1R knockout mice (FIG. 4(B)) compared with that observed in cultures from wildtype mice (FIG. 4(A)). Maximal levels of neurite outgrowth generated by high dose (HD) growth factors were the same between cultures from wild type mice (FIG. 4(A)) and knockout mice (FIG. 4(B)). Pirenzepine treatments increased neurite outgrowth 2-fold compared with LD control in cultures from wildtype mice (FIG. 4(A)). However, pirenzepine treatments did not enhance neurite outgrowth in cultures from M1R knockout mice (FIG. 4(B)). Also measured were the amounts of acetylcholine produced by the DRG sensory neuron cultures. FIG. 5 shows that the M1R knockout mice sensory neuron cultures produced significantly less acetylcholine compared to the wildtype cultures. These data suggest that, at least in acute cell culture conditions, sensory neurons self-limit their axonal outgrowth via an autocrine cholinergic pathway (presumably through an acetylcholine/M1R dependent pathway). The surprising ability of M1R antagonists or genetic removal of the M1R to accelerate axonal outgrowth has prompted the hypothesis that adult peripheral neurons are under constant "cholinergic constraint" that prevents excessive growth once they have attained contact with their target. With regard to innervation of the epidermis by sensory fibers keratinocytes secrete acetylcholine and communicate via a non-neuronal network of cholinergic receptors that has importance during wound repair. The presence of M1Rs on sensory neurons offers the intriguing possibility that neurons themselves and/or keratinocytes use acetylcholine as the "stop" signal for preventing uncontrolled fiber growth.

Example 5: Effects of Pirenzepine on Phosphorylation of Extracellular-Regulated Protein Kinase (ERK) in Cultured Sensory Neurons Lumbar DRG were isolated from male out-bred Sprague Dawley rats generally following the method outlined in Example 1, and then were cultured for 24 h in serum-free and insulin-free F12 medium in the presence of modified N2 additives plus 10 pirenzepine. Samples were taken immediately (time 0) and then after 15 min, 30 min, 6 hr, and 24 hr of incubation. Quantitative Western blotting was performed as taught by Chowdhury et al (2010) and Fernyhough et al. (1999, Diabetes 48: 881-889). DRG homogenates of 5-10 µg of protein were resolved on a 10% SDS-PAGE gel and electroblotted onto nitrocellulose membrane. Blots were then blocked in 5% nonfat milk containing 0.05% Tween-20, rinsed in PBS (pH 7.4) and incubated with an antibody reagent specific to phosphorylated (Thr-202/Tyr-204) or total extracellular signal-regulated kinase (P-ERK or T-ERK; 1:4000 and 1:2000, respectively; Covance, Princeton, NJ, US). The blots were rinsed, incubated in Western blotting Luminol Reagent (Santa Cruz Biotechnology Inc., Santa Cruz, CA, US) and imaged using a BioRad Fluor-S image analyzer (BioRad, Hercules, CA, US). The data in FIGS. 6(A) and 6(B) show that pirenzepine elevated phosphorylation of ERK (P-ERK) by approximately 2-fold after 15 min with a return to baseline by 24 hr (relative to total ERK levels).

Example 6: Effects of a M1R Muscarinic Antagonist VU255035 on AMP-Activated Protein Kinase (AMPK) Activity in Cultured Sensory Neurons Lumbar DRG were isolated from male out-bred Sprague Dawley rats generally following the method outlined in Example 1, and then were cultured for 6 h in serum-free and insulin-free F12 medium in the presence of modified N2 additives plus 10 µM VU255035. Samples were taken immediately (time 0) and then after 15 min, 30 min, 60 min, and 6 hr of incubation. Quantitative Western blotting was performed as following the procedure taught in Example 5. DRG homogenates of 5-10 µg of protein were resolved on a 10% SDS-PAGE gel and electroblotted onto nitrocellulose membrane. Blots were then blocked in 5% nonfat milk containing 0.05% Tween-20, rinsed in PBS (pH 7.4) and incubated with the following antibodies: (i) polyclonal anti-phospho AMPK (on Thr-172, 1:1000, Cell Signaling Technology, Danvers, MA, US), and (ii) extracellular signal-regulated kinase (T-ERK; 1:2000, Covance, Princeton, NJ, US). The blots were rinsed, incubated in Western blotting Luminol Reagent (Santa Cruz Biotechnology Inc., Santa Cruz, CA, US) and imaged using a BioRad Fluor-S image analyzer (BioRad, Hercules, CA, US). The data in FIGS. 7(A) and 7(B) show that VU255035 significantly raised phosphorylation of AMPK (P-AMPK) by 15 min and maintained phosphorylation at 30-60 min with a return to baseline by 6 hr (relative to total ERK levels; total AMPK levels were not affected).

Example 7: Prophylactic Effects of Subcutaneous Injections of Pirenzepine on the Development of Symmetrical Polyneuropathy in a Mouse Model of Type 1 Diabetes Mouse Male C57B16J mice were made diabetic with 2 injections of 90 mg/kg STZ on consecutive days, and then separated into four groups. A fifth group was the control (non-diabetic) group and comprised mice that did not receive the STZ injections. The first group of diabetic mice did not receive any pirenzepine treatments during the course of the two-month study and serve to illustrate the neuropathy induced by diabetes. The first group of STZ diabetic mice developed signs of neuropathy, including nerve conduction slowing, thermal hypoalgesia and IENF loss within 2 months of the STZ treatments. The second, third and fourth groups of STZ diabetic mice received daily pirenzepine treatments administered by subcutaneous injection at the scruff of the neck, starting one week after the second STZ injection. The second group of STZ diabetic mice received a daily dose of 0.1 mg pirenzepine/kg body weight. The third group of STZ diabetic mice received a daily dose of 1.0 mg pirenzepine/kg body weight. The fourth group of STZ diabetic mice received a daily dose of 10.0 mg pirenzepine/kg body weight.

Two months after the second STZ injection, the function of the small sensory neurons in all five groups of mice were determined by measuring hind paw thermal response latency using a modified Hargreaves apparatus (UARD, San Diego, CA, US) with a heating rate of approximately 1° C./sec from a baseline of 30° C. and with a cut-off at 20 seconds as taught by Calcutt et al. (2004, Diabetologia 47: 718-724). The data in FIG. 8(A) show that the group of STZ diabetic mice that were otherwise untreated demonstrated a significant increase in thermal latency in comparison to the control (non-diabetic) mice. The group of diabetic mice receiving daily pirenzepine subcutaneous injections at 10 mg/kg showed a thermal response latency that was not significantly different from the control non-diabetic mice (FIG. 8(B)). Statistical analysis was done using the one-way ANOVA with post-hoc comparison using Tukey's test.

The structural integrity of small sensory neurons was assessed by measuring intraepidermal nerve fiber (IENF) profiles in hind paw plantar skin that was immersion fixed in 4% paraformaldehyde and processed to paraffin blocks. Sections (6 µm) were stained with the pan-neuronal marker PGP9.5 (1:1000, Biogenesis Ltd., Poole, UK) and viewed under a light microscope to allow counting of IENF and sub-epidermal nerve profiles (SNP) per unit length of the dermal: epidermal border using the technique taught by Beiswenger et al. (2008, Neurosci Lett. 442, 267-272). The data in FIGS. 8(A) and 8(B) show that the STZ-diabetic mice that were otherwise untreated demonstrated a significant decrease in the paw levels of IENF in comparison to the control (non-diabetic mice). The group of diabetic mice receiving daily subcutaneous injections of 10 mg/kg pirenzepine demonstrated no significant changes in the paw levels of IENF compared to the control (non-diabetic) mice. Statistical analyses were done using one-way ANOVA followed by Tukey's test.

Motor nerve conduction velocity was measured under isoflurane anesthesia and core and nerve temperature were maintained at 37° C. using a heating pad and lamps following the teachings of Jolivalt et al, (2011, Diabetes Obesity and Metabolism, June 2 Epub ahead of print). The sciatic nerve was stimulated (5V, 0.05 ms pulse, square wave) with needle electrodes at the sciatic notch or ankle. Evoked early (M waves) responses were recorded from interosseous muscles of the foot with fine needle electrodes, amplified and displayed on an oscilloscope. The difference in response latencies of the M wave after stimulation at the sciatic notch and ankle was recorded as the time required for the motor nerve conduction between the stimulation sites. The distance between stimulation sites was measured on the surface of the fully extended hind limb and divided by the difference in M wave latencies to calculate sciatic motor nerve conduction velocity (MNCV). Measurements were made in triplicate and the median value used to represent MNCV for each animal.

Example 8: Reversal of Thermal Hypoalgesia and IENF Loss in STZ-Induced Diabetic Mice with VU255035

Swiss Webster (outbred) mice were made diabetic with 2 injections of 90 mg/kg STZ on consecutive days. A control group of age matched Swiss Webster mice did not receive the STZ injections. The mice were maintained for 8 weeks after STZ injections. Diabetic neuropathy was well-established in the mice that received STZ injections as evidenced by signs of neuropathy (thermal hypoalgesia). A cohort then received 10 mg/kg VU255035 by i.p. injection daily for 4 weeks. The data in FIG. 9(A) show that thermal hypoalgesia (sensory loss) had developed by 8 weeks and treatment with VU255035 caused a significant reversal back to control levels of thermal sensitivity. FIG. 9(B) shows that VU255035 also significantly reversed loss of IENF and SNP.

Example 9: Prophylactic Effects of Topical Application of Pirenzepine on the Development of Sensory Neuropathy in a Mouse Model of Type 1 Diabetes Male C57Bl6J mice were made diabetic with 2 injections of 90 mg/kg STZ on consecutive days, and then separated into three groups. There were also two groups control (non-diabetic) mice. The first group of control (non-diabetic) mice received daily topical treatment with 50 µl Intrasite® hydrogel (Intrasite is a registered trademark of T. J. Smith and Nephew, Hull, England) to both hind paws, with a controlled exposure time of 20 minutes. The second group of control (non-diabetic) mice received a daily topical application of 50 µl of a gel composition comprising 10% pirenzepine in hydrogel to one hind paw and 50 µl hydrogel alone to the other paw, commencing when the diabetic mice received their topical treatments. The third group of mice were diabetic mice that received daily topical treatment with 50 µl hydrogel to both hind paws. The fourth group comprised diabetic mice that received a daily topical application of 50 µl of hydrogel comprising 2% pirenzepine to one hind paw and 50 µl hydrogel alone to the other hind paw, treatment commencing 7 days after the second STZ injection. The fifth group comprised diabetic mice that received a daily topical application of 50 µl hydrogel comprising 10% pirenzepine to one hind paw and 50 µl hydrogel alone to the other hind paw, treatment commencing 7 days after the second STZ injection. The group of STZ diabetic mice treated with hydrogel alone to both hindpaws developed signs of neuropathy, including nerve conduction slowing, thermal hypoalgesia and IENF loss within 2 months of the STZ treatments.

Two months after the second STZ injection, the function of the small sensory neurons in all five groups of mice were determined by measuring hind paw thermal response latency following the procedure described in Example 7. The data in FIG. 10(A) show that thermal response latency in control (non-diabetic) mice was not affected by a daily topical application of the hydrogel comprising 10% pirenzepine. STZ diabetic mice treated with hydrogel alone to both hindpaws demonstrated a significant increase in thermal response latency in comparison to both groups of control (non-diabetic) mice. The two groups of diabetic mice receiving daily topical applications of pirenzepine hydrogel to one hindpaw did not demonstrate any significant changes in thermal response latency in that paw when compared to the control (non-diabetic) mice (statistical analysis was done using the one-way ANOVA with post-hoc comparison using Tukey's test).

The structural integrity of small sensory neurons was assessed by measuring IENF profiles in hind paw plantar skin as described in Example 7. The data in FIGS. 10(B) and 10(C) show that application of hydrogel comprising 10% pirenzepine to one hind paw of control (non-diabetic) mice resulted in numerically, but statistically insignificant, increases in IENF and SNP per mm of skin taken from the pirenzepine-treated hindpaw. The STZ diabetic mice treated with hydrogel alone to both hind paws demonstrated a significant decrease in the paw levels of IENF and SNP per mm of skin in comparison to the control (non-diabetic) mice that were treated with hydrogel alone to both hind paws. The two groups of diabetic mice receiving daily topical applications of 50 µl hydrogel comprising 2% or 10% pirenzepine demonstrated no significant changes in the levels of IENF and SNP in the paw treated with pirenzepine when compared to the control (non-diabetic mice) that were treated with hydrogel alone to both hind paws (statistical analysis was done using the one-way ANOVA with post-hoc comparison using Tukey's test).

Example 10: Restorative Effects of Subcutaneous Injections of Pirenzepine on Thermal Hypoalgesia and IENF Loss in Diabetic Mice Male out-bred Swiss Webster mice were made diabetic with 2 injections of 90 mg/kg STZ on consecutive days. A control group of age matched Swiss Webster mice did not receive the STZ injections. The mice were maintained for 14 weeks after STZ injections. Diabetic neuropathy was well-established in the mice that received STZ injections as evidenced by signs of neuropathy, thermal hypoalgesia and IENF loss. At 14 weeks, the diabetic mice were separated into two groups. The first was the untreated group of diabetic mice. The other group of diabetic mice received daily subcutaneous injections of pirenzepine at a dose of 10 mg/kg for 2 months.

The function of the small sensory neurons in diabetic and non-diabetic groups of mice were assessed at 5 wks, 7 wks, 11 wks, and 14 wks after the STZ injections. There was a significant increase in thermal latency in the diabetic mice compared to non-diabetic mice, following the procedure described in Example 7. Hypoalgesia was observed 11 weeks after the STZ injections and became even more pronounced at 14 weeks (FIG. 11(A)). Microscopic examination of skin tissue samples collected from the diabetic mice at 14 weeks showed approximately a 40% loss in IENF.

However, daily pirenzepine administrations to diabetic mice significantly reduced thermal latency within 4 weeks of commencing the pirenzepine treatment, i.e., at 18 weeks (FIG. 11(A)) and by the 21$^{st}$ week i.e., 7 weeks after commencing the pirenzepine treatments, the thermal latency in the diabetic mice was identical to the non-diabetic controls (FIG. 11(A)). Determination of the IENF profiles in the three groups of mice at 21-weeks demonstrated that application of the pirenzepine treatments to diabetic mice restored the IENF profiles to approximate those of the non-diabetic control mice (FIG. 11 (B)).

Example 11: Reappearance of Neuropathy after Withdrawal of Pirenzepine Treatments C57Bl6J mice were made diabetic with STZ as previously described and then received 10 mg/kg pirenzepine (daily subcutaneous injections). After 8 weeks, hypoalgesia was prevented by the pirenzepine treatments (FIG. 12). At this juncture, the pirenzepine treatments were stopped and thermal latencies measured every two weeks thereafter (FIG. 12). Only 9 weeks later (the 17-wk time point) was there a significant reappearance of hypoalgesia in the previously treated STZ-induced diabetic mice (FIG. 12).

Example 12: Reversal Effects of Subcutaneous Injections of Pirenzepine on the Thermal Hypoalgesia in Diabetic Rats One group of adult male Sprague Dawley rats were made diabetic with a single intraperitoneal injection of 75 mg/kg STZ, while a second group of adult male rats were maintained as non-diabetic controls. The two groups of rats were monitored for the onset of type 1 diabetes by assessing thermal latency at 4-wk intervals. By week 12, neuropathy was well established in the STZ-treated rats (FIG. 13). The diabetic rats were then separated into two groups, with one group of rats each receiving a daily subcutaneous injection of 10 mg/kg of pirenzepine. Assessments of thermal latency continued at 4-wk intervals, and by the 20$^{th}$ week of the study, i.e., 8 weeks after the daily pirenzepine injections commenced, the thermal latency in the diabetic rats receiving the injections had dropped to approximate the levels in the non-diabetic control rats (FIG. 13).

Example 13: Effects of Pirenzepine on Preventing Development of Pain, Indicated by Tactile Allodynia, and Sensory Nerve Conduction Slowing in Diabetic Rats Two groups of adult female Sprague Dawley rats were made diabetic with a single intraperitoneal injection of 55 mg/kg STZ. One of the two groups of STZ-injected rats received daily treatments of 10 mg/kg pirenzepine by subcutaneous injection, while the second group received injections of vehicle alone. A third group of adult male rats was maintained as non-diabetic controls. The three groups of rats were monitored for the onset of diabetic painful neuropathy by measuring paw tactile response thresholds at weeks 5 and 9 of diabetes, as taught by Calcutt (1996, Pain: 68:293-299). Painful neuropathy, as indicated by tactile allodynia (50% response threshold below 5 g) was well established by week 5 in the STZ-treated rats that did not receive the pirenzepine treatments and persisted for up to 9 weeks of diabetes. Pirenzepine treated diabetic rats had paw tactile response thresholds that were significantly higher than vehicle treated diabetic rats after 5 weeks of diabetes (FIG. 14(A)) and not different from control rats by week 9 of diabetes (FIG. 14(A)). Sensory nerve conduction velocity (SNCV) was measured in the same cohorts of rats after 8 weeks of diabetes by measuring under isoflurane anesthesia, the latency of H waves in the electromyogram of interosseous muscles following electrical stimulation of the sciatic nerve at the sciatic notch and Achilles tendon and then measuring the distance between the two points of nerve stimulation, as taught by Calcutt (J. Clin. Invest. 111:507-514, 2003). SNCV was significantly reduced in diabetic rats and pirenzepine partially prevented this deficit (FIG. 14(B)).

Example 14: Reversal of Diabetic Sensory Neuropathy with Oral Dosing of Pirenzepine Male out-bred Swiss Webster mice were made diabetic with 2 injections of 90 mg/kg STZ on consecutive days. A control group of age matched Swiss Webster mice did not receive the STZ injections. The mice were maintained for 8 weeks after STZ injections. Diabetic neuropathy was well-established in the mice that received STZ injections as evidenced by signs of thermal hypoalgesia. At 8 weeks, daily pirenzepine treatments were delivered to a sub-group of the STZ-diabetic mice by oral gavage for a further 8-week period. The data in FIG. 15(A) show that treatments delivering pirenzepine orally reversed thermal hypoalgesia. In addition, oral dosing with pirenzepine also reversed loss of IENF and SNP (FIG. 15(B)).

Example 15: Assessment of Pirenzepine Effects on Gene Expression of AMPK and PGC1α in Dorsal Root Ganglia (DRG) in STZ-Diabetic Mice Some of the mice in each of the three groups of mice (non-diabetic control group; diabetic untreated group; diabetic group receiving daily pirenzepine injections from the 14$^{th}$ week onward) from the study described in Example 10 were maintained through 22 weeks after the STZ injections. Lumbar DRG were isolated and rinsed in ice-cold solution containing STE buffer (250 mmol/l sucrose, 10 mmol/l Tris-HCl, 1 mmol/l EDTA, pH 7.4), and then homogenized with a polytron homogenizer (KINEMATICA GmbH, Switzerland) using 3×7.5 s grinding pulses at 30 s intervals according to the method taught by Chowdhury et al. (2010, Diabetes 59: 1082-1091).

Quantitative Western blotting was performed as previously disclosed by Chowdhury et al (2010) and Fernyhough et al. (1999, Diabetes 48: 881-889). DRG homogenates of 5-10 μg of protein were resolved on a 10% SDS-PAGE gel and electroblotted onto nitrocellulose membrane. Blots were then blocked in 5% nonfat milk containing 0.05% Tween-20, rinsed in PBS (pH 7.4) and incubated with the following antibodies: polyclonal anti-phospho AMPK (1:1000, Cell Signaling Technology, Danvers, MA, US), polyclonal anti-PGC-1α (1:1000, Santa Cruz Biotechnology Inc, Santa Cruz, CA, USA) and monoclonal anti-ATP synthase β subunit (1:2000 dilution, Mitosciences, Eugene, OR). Extracellular signal-regulated kinase (ERK; 1:2000, Covance, Princeton, NJ, US) was probed as a loading control (previous studies show this protein to not change level of expression in DRG in diabetes). The blots were rinsed, incubated in Western blotting Luminol Reagent (Santa Cruz Biotechnology Inc., Santa Cruz, CA, US) and imaged using a BioRad Fluor-S image analyzer (BioRad, Hercules, CA, US).

The data in FIGS. 16(A)-16(D) show that gene expression of P-AMPK, T-AMPK, and PGC-1α was reduced in diabetic mice compared to the non-diabetic controls, and that daily subcutaneous injections of pirenzepine for 8 weeks restored the expression of these genes.

Example 16: Assessment of Pirenzepine Effects on Expression of Mitochondrial Respiratory Complex Proteins in Dorsal Root Ganglia in STZ-Diabetic Mice The DRG samples were assessed for the expression of specific mitochondrial proteins in diabetic rats that received daily injections of pirenzepine for 8 weeks. Quantitative Western blotting was performed as described in Example 15. Quantitative Western blotting was performed as previously disclosed by Chowdhury et al (2010) and Fernyhough et al. (1999). DRG homogenates of 5-10 µg of protein were resolved on a 10% SDS-PAGE gel and electroblotted onto nitrocellulose membrane. Blots were then blocked in 5% nonfat milk containing 0.05% Tween-20, rinsed in PBS (pH 7.4) and incubated with the following antibodies: monoclonal anti-cytochrome c oxidase subunit 4 (COX IV; 1:1000, Mitosciences, Eugene, OR, US), monoclonal anti-NADH dehydrogenase (ubiquinone) iron-sulfur protein 3 (NDUFS3, 1:1000, Mitosciences, Eugene, OR, US). Extracellular signal-regulated kinase (T-ERK; 1:2000, Covance, Princeton, NJ, US) was probed as a loading control. The blots were rinsed, incubated in Western blotting Luminol Reagent (Santa Cruz Biotechnology Inc., Santa Cruz, CA, US) and imaged using a BioRad Fluor-S image analyzer (BioRad, Hercules, CA, US).

The data in FIGS. 17(A)-17(C) demonstrate that pirenzepine treatments restored the expression of NDUFS3 and COX IV mitochondrial proteins.

Example 17: Assessment of Pirenzepine Effects on Activity of Mitochondrial Respiratory Complexes in Dorsal Root Ganglia in STZ-Diabetic Mice The samples of lumbar DRG from mice described in Example 10 were assessed for the restoration of activity of mitochondrial complexes in diabetic mice that received daily injections of pirenzepine for 8 weeks.

All measurements of enzymatic activities in lumbar DRG preparations were performed spectrophotometrically using a temperature controlled Ultrospec 2100 UV-visible spectrophotometer (Biopharmacia Biotech, Uppsala, Sweden) using the methods taught by Chowdhury et al. (2010). Complex I activity was measured as rotenone-sensitive NADH: cytochrome c reductase activity. Freshly prepared assay buffer (50 mmol/l K-phosphate pH 7.4, 1 mmol/l KCN, 100 µmol/l NADH) and 10 µg protein of DRG homogenate preparation were added to the cuvette and preincubated for 3 min at 25° C. After addition of 100 µmol/l oxidized cytochrome c, the reaction was followed for 2 minutes at 550 nm and then for 2 more minutes after addition of 25 µmol/l rotenone to allow calculation of the rotenone-sensitive Complex I activity. Complex IV activity was measured at 25° C. by monitoring the absorbance decrease of reduced cytochrome c at 550 nm as disclosed by Chowdhury et al. (2000, Clin. Chim. Acta 298: 157-173). The reaction was started by addition of 40 µmoil reduced cytochrome c into 50 mmol/l phosphate buffer containing 5 µg of protein solubilized with 0.02% laurylmaltoside. Activity of the Krebs cycle enzyme, citrate synthase, was determined at 25° C. in medium containing 150 mmol/l Tris-HCl (pH 8.2), 0.02% laurylmaltoside, 0.1 mmol/l dithionitrobenzoic acid and 5 µg protein according to the method of Chowdhury et al (2007, Free Radic. Res. 41: 1116-1124). The reaction was initiated by addition of 100 µmol/l acetyl CoA and changes in absorbance at 412 nm were measured for 1 minute. This value was subtracted from the rate obtained after addition of 0.05 mmol/l oxaloacetic acid.

The data in FIGS. 18(A)-18(C) demonstrate that pirenzepine treatments restored the deficits in mitochondrial respiratory complexes I and IV, and in citrate synthase.

Example 18: Assessment of Pirenzepine Effects on Mitochondrial Respiratory Chain Activity in Freshly Homogenized Lumbar Dorsal Root Ganglia in STZ-Diabetic Rats Some of the rats in each of the three groups of rats (non-diabetic control group; diabetic untreated group; diabetic group receiving daily pirenzepine injections from the 14th week onward) from the study described in Example 12 were maintained through 20 weeks after the STZ injections. The rats were then culled and subsequently the lumbar DRG were isolated and rinsed in ice-cold solution containing STE buffer (250 mmol/l sucrose, 10 mmol/l Tris-HCl, 1 mmol/l EDTA, pH 7.4), and then homogenized with a polytron homogenizer (KINEMATICA GmbH, Switzerland) using 3×7.5 s grinding pulses at 30 s intervals according to the method taught by Chowdhury et al. (2010).

Mitochondrial respiratory chain activity in freshly isolated mitochondria from lumbar DRG of age-matched control, diabetic, and pirenzepine-treated diabetic rats was determined using a Clarke-type electrode (Oroboros Oxygraph-2K; Oroboros Instruments, Innsbruck, Austria) following the method taught by Chowdhury et al. (2005, Biochem Biophys Res Commun. 333: 1139-1145), in the presence of specific substrates and inhibitors of the mitochondrial respiratory chain (FIG. 19). Basal respiration in lumbar DRG mitochondria is stated as respiration at state 4 with energetic substrates, pyruvate and malate (P+M). Coupled respiration at state 3 was induced by addition of ADP. Then, the uncoupled rate was determined by adding the uncoupling agent, carbonylcyanide p-trifluoromethoxy-phenylhydrazone (FCCP). Ascorbate (Asc) and N,N,N',N'-tetramethyl-p-phenylenediamine (TMPD) were then added to determine the capacity of cytochrome c oxidase (complex IV). TMPD is an artificial redox mediator that assists transfer of electrons from ascorbate to cytochrome c.

Basal respiration rates with pyruvate and malate (P+M) were similar for the control non-diabetic rats, diabetic rats, and in the diabetic rats that had received daily sub-cutaneous injections of pirenzepine daily during the last eight weeks of the study (FIG. 19). Coupled respiration in diabetic rats after 20 weeks was decreased about 30% from the control non-diabetic rats (P+M+ADP). However, coupled respiration in diabetic rats that had received daily sub-cutaneous injections of pirenzepine, was not significantly different from the non-diabetic controls. While uncoupled respiration in diabetic rats after 20 weeks decreased about 40% from the control non-diabetic rats (FCCP), uncoupled respiration in diabetic rats that had received daily sub-cutaneous injections of pirenzepine, was not significantly different from the non-diabetic controls. The capacity of cytochrome c oxidase (complex IV) in diabetic rats after 20 weeks was decreased about 25% from the control non-diabetic rats (Asc+TMPD). However, capacity of the cytochrome c oxidase in diabetic rats that had received daily sub-cutaneous injections of pirenzepine, was not significantly different from the non-diabetic controls.

Example 19: Preparation of a Pirenzepine Composition for Topical Application

A pirenzepine composition for topical application was prepared by mixing 10 mg pirenzepine powder into 0.5 ml of a suitable gel for a 2% (20 mg/ml) gel. A suitable gel is exemplified by Intrasite® sterile hydrogel prod. no. 66027313 (Smith & Nephew Inc, St. Laurent, PQ, CA). Alternatively, 100 mg of pirenzepine powder can be mixed into 1.0 ml of gel to prepare a 10% (100 mg/ml) gel.

Example 20: Preparation of Oral Formulation of Pirenzepine

Pirenzepine (either in its hydrochloride form or its hydrate form or other similar salt forms) can be either dissolved in saline, distilled water, or in a suitable tablet formulation for oral delivery. Such formulations can be prepared using the general knowledge available on pirenzepine or its various salt forms in the literature and by someone with the reasonable knowledge of the art. A formulation of pirenzepine hydrochloride dissolved in water and administered orally to mice exhibited efficacy (FIGS. 15(A) and 15(B)).

The invention claimed is:

1. A method of treating diabetic peripheral neuropathy in a subject in need thereof, the method comprising:
    administering a composition comprising an effective amount of a selective muscarinic acetylcholine M1 receptor antagonist selective for the M1 receptor wherein such administration reduces diabetic peripheral neuropathy in the subject.

2. The method of claim 1, wherein said treatment increases neurite outgrowth in the subject.

3. The method of claim 1, wherein administering the composition comprises administering the composition daily.

4. The method of claim 3, wherein administering the composition comprises administering the composition daily for eight weeks.

5. The method of claim 1, wherein the selective muscarinic acetylcholine M1 receptor antagonist is selected from the group consisting of: VU255035, pirenzepine, telenzepine, atropine, oxybutynin, MT7, PD150714, trihexyphenidyl, p-fluotrihexyphenidyl, O-methoxy-sila-hexocyclium, spirotramine, McN-A-343, McN-A-343 analog, MB-OXTP, nitrocaramiphen, aprophen, (−)-S-ET126, N-desmethylclozapine, MDL74019DG, glycopyrronium bromide, dicyclomine, and salts thereof.

6. The method of claim 5, wherein the selective muscarinic acetylcholine M1 receptor antagonist is pirenzepine or a salt thereof.

7. The method of claim 5, wherein the selective muscarinic acetylcholine M1 receptor antagonist is telenzepine, oxybutynin, atropine or salts thereof.

8. The method of claim 1, wherein the administration comprises a topical administration, oral delivery, subcutaneous injection, or intravenous injection.

9. The method of claim 8, wherein the topical administration comprises a topical administration of pirenzepine.

10. The method of claim 9, wherein the topical administration comprises topical administration of a lotion, cream or gel to the subject.

11. The method of claim 9, wherein the topical administration of pirenzepine comprises administration of pirenzepine with a skin penetration enhancing agent.

12. The method of claim 11, wherein the skin penetration enhancing agent is at least 0.1% by weight of the composition.

13. The method of claim 11, wherein the skin penetration enhancing agent comprises a sulfoxide, an alkanone or a linear fatty acid.

14. The method of claim 13, wherein the linear fatty acid is a linoleic acid.

15. The method of claim 11, wherein the skin penetration enhancing agent is a non-cationic skin penetration enhancing agent.

16. The method of claim 11, wherein the composition further comprises at least one of a thickening agent, an emollient, an antioxidant, an antimicrobial preservative.

17. The method of claim 11, wherein the topical administration is through a transdermal patch.

18. The method of claim 1, wherein the diabetic peripheral neuropathy comprises diabetic sensory neuropathy.

19. A method of treating diabetic peripheral neuropathy in a subject in need thereof, the method comprising administering a composition comprising an effective amount of a selective muscarinic acetylcholine M1 receptor antagonist selective for the M1 receptor,
    wherein administration comprises topical application;
    wherein the composition is provided as a lotion, cream or gel; and
    wherein administration reduces diabetic peripheral neuropathy in the subject.

20. A method of treating diabetic peripheral neuropathy in a subject in need thereof, the method comprising administering a composition comprising an effective amount of a selective muscarinic acetylcholine M1 receptor antagonist selective for the M1 receptor, wherein administration reduces diabetic peripheral neuropathy in the subject,
    wherein the selective muscarinic acetylcholine M1 receptor antagonist is selected from the group consisting of: VU255035, pirenzepine, telenzepine, atropine, MT7, PD150714, trihexyphenidyl, p-fluotrihexyphenidyl, O-methoxy-sila-hexocyclium, spirotramine, McN-A-343, McN-A-343 analog, MB-OXTP, nitrocaramiphen, aprophen, (−)-S-ET126, N-desmethylclozapine, MDL74019DG, glycopyrronium bromide, dicyclomine, and salts thereof; and
    wherein administration comprises topical application, oral delivery, subcutaneous injection, or intravenous injection.

21. A method of treating diabetic peripheral neuropathy in a subject in need thereof, the method comprising:
    administering a composition comprising an effective amount of a selective muscarinic M1 acetylcholine antagonist selective for the M1 receptor wherein such administration reduces diabetic peripheral neuropathy in the subject.

22. The method of claim 21, wherein the selective muscarinic M1 acetylcholine antagonist is selected from the group consisting of: VU255035, pirenzepine, telenzepine, atropine, oxybutynin, MT7, PD150714, trihexyphenidyl, p-fluotrihexyphenidyl, O-methoxy-sila-hexocyclium, spirotramine, McN-A-343, McN-A-343 analog, MB-OXTP, nitrocaramiphen, aprophen, (−)-S-ET126, N-desmethylclozapine, MDL74019DG, glycopyrronium bromide, dicyclomine, and salts thereof.

23. The method of claim 21, wherein the selective muscarinic M1 acetylcholine antagonist is pirenzepine or a salt thereof.

24. The method of claim 21, wherein the selective muscarinic M1 acetylcholine antagonist is telenzepine, oxybutynin, atropine or salts thereof.

25. The method of claim 21, wherein the administration comprises a topical administration, oral delivery, subcutaneous injection, or intravenous injection.

26. The method of claim 25, wherein the topical administration comprises a topical administration of pirenzepine.

27. The method of claim 26, wherein the topical administration comprises topical administration of a lotion, cream or gel to the subject.

\* \* \* \* \*